United States Patent
Pivonka et al.

(10) Patent No.: US 11,633,151 B2
(45) Date of Patent: Apr. 25, 2023

(54) METHOD AND APPARATUS FOR VERSATILE MINIMALLY INVASIVE NEUROMODULATORS

(71) Applicant: Nalu Medical, Inc., Carlsbad, CA (US)

(72) Inventors: Daniel Pivonka, Palo Alto, CA (US); Anatoly Yakovlev, Santa Clara, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 859 days.

(21) Appl. No.: 16/266,822

(22) Filed: Feb. 4, 2019

(65) Prior Publication Data
US 2019/0269913 A1 Sep. 5, 2019

Related U.S. Application Data

(63) Continuation of application No. 15/264,864, filed on Sep. 14, 2016, now Pat. No. 10,238,872, which is a (Continued)

(51) Int. Cl.
*A61B 5/00* (2006.01)
*A61N 1/372* (2006.01)
(Continued)

(52) U.S. Cl.
CPC .......... *A61B 5/4836* (2013.01); *A61B 5/6871* (2013.01); *A61N 1/36007* (2013.01);
(Continued)

(58) Field of Classification Search
CPC ............ A61N 1/37205; A61N 1/37223; A61N 1/36007; A61N 1/36053; A61N 1/36064;
(Continued)

(56) References Cited

U.S. PATENT DOCUMENTS 6,516,227 B1 * 2/2003 Meadows .......... A61N 1/36071
607/46
8,504,138 B1 8/2013 Pivonka et al.
(Continued)

FOREIGN PATENT DOCUMENTS

WO WO-2014071079 A1 5/2014
WO WO-2014205129 A1 12/2014
(Continued)

OTHER PUBLICATIONS

U.S. Appl. No. 15/264,864 Notice of Allowance dated Nov. 8, 2018.
(Continued)

*Primary Examiner* — Mallika D Fairchild
(74) *Attorney, Agent, or Firm* — Cooley LLP

(57) ABSTRACT

A medical apparatus configured to neuromodulate tissue and/or record patient information is provided. The apparatus includes an external system to transmit transmission signal(s), each signal having at least power or data, and an implantable system to receive the transmission signal(s). The data transfer between the external and implantable systems is asynchronous. The external system includes external antenna(s) to transmit a transmission signal. The transmission signal is an amplitude modulated signal modulated by varying a load on the external antenna(s) that causes an impedance mismatch prior to amplifying the signal for transmission. An implantable device includes implantable antenna(s) to receive the transmission signal. The implantable system comprises a receiver to receive the transmission signal from the implantable antenna(s), implantable transmission module(s) to transmit data to the external system, and a variable load connected to the implantable antenna(s). Data is transmitted by varying the load.

22 Claims, 15 Drawing Sheets

Related U.S. Application Data continuation of application No. PCT/US2015/020808, filed on Mar. 16, 2015.

(60) Provisional application No. 61/953,702, filed on Mar. 14, 2014.

(51) Int. Cl.
*A61N 1/36* (2006.01)
*A61N 1/378* (2006.01)
*A61N 1/05* (2006.01)

(52) U.S. Cl.
CPC ....... *A61N 1/3614* (2017.08); *A61N 1/36053* (2013.01); *A61N 1/36062* (2017.08); *A61N 1/36064* (2013.01); *A61N 1/36067* (2013.01); *A61N 1/36071* (2013.01); *A61N 1/36075* (2013.01); *A61N 1/36125* (2013.01); *A61N 1/3787* (2013.01); *A61N 1/37205* (2013.01); *A61N 1/37223* (2013.01); *A61B 5/4824* (2013.01); *A61B 2560/0219* (2013.01); *A61F 2250/0001* (2013.01); *A61N 1/0534* (2013.01); *A61N 1/0551* (2013.01); *A61N 1/37229* (2013.01)

(58) Field of Classification Search
CPC ............ A61N 1/36067; A61N 1/36071; A61N 1/36075; A61N 1/36125; A61N 1/3787; A61N 1/0534; A61B 5/4836; A61B 5/6871
See application file for complete search history.

(56) References Cited

U.S. PATENT DOCUMENTS

| | | | |
|---|---|---|---|
| 8,538,541 B2 | 9/2013 | Milojevic et al. | |
| 8,634,928 B1 | 1/2014 | O'Driscoll et al. | |
| 8,655,451 B2 | 2/2014 | Klosterman et al. | |
| 9,433,750 B2 | 9/2016 | Pivonka et al. | |
| 10,238,872 B2 | 3/2019 | Pivonka et al. | |
| 10,320,232 B2 | 6/2019 | Pivonka et al. | |
| 10,335,596 B2 | 7/2019 | Yakovlev et al. | |
| 10,411,760 B2 | 9/2019 | Yakovlev et al. | |
| 10,644,539 B2 | 5/2020 | Pivonka et al. | |
| 10,849,643 B2 | 12/2020 | Castillo et al. | |
| 10,898,719 B2 | 1/2021 | Pivonka et al. | |
| 10,967,183 B2 | 4/2021 | Yakovlev et al. | |
| 11,018,721 B2 | 5/2021 | Yakovlev et al. | |
| 11,090,491 B2 | 8/2021 | Mishra et al. | |
| 11,097,096 B2 | 8/2021 | Linden et al. | |
| 11,133,709 B2 | 9/2021 | Pivonka et al. | |
| 11,160,980 B2 | 11/2021 | Mishra et al. | |
| 2007/0213773 A1* | 9/2007 | Hill .................... A61N 1/36114 607/2 |
| 2009/0105782 A1 | 4/2009 | Mickle et al. | |
| 2010/0137948 A1* | 6/2010 | Aghassian ......... A61N 1/37235 607/61 |
| 2011/0137378 A1 | 6/2011 | Klosterman et al. | |
| 2011/0190849 A1 | 8/2011 | Faltys et al. | |
| 2011/0276110 A1 | 11/2011 | Whitehurst et al. | |
| 2012/0197352 A1 | 8/2012 | Carbunaru et al. | |
| 2013/0023943 A1 | 1/2013 | Parramon et al. | |
| 2013/0053767 A1 | 2/2013 | Pivonka et al. | |
| 2013/0079861 A1 | 3/2013 | Reinert et al. | |
| 2013/0211469 A1 | 8/2013 | Lamont et al. | |
| 2013/0215979 A1* | 8/2013 | Yakovlev ............. H04B 5/0037 375/256 |
| 2013/0261703 A1 | 10/2013 | Chow et al. | |
| 2013/0265144 A1* | 10/2013 | Banna ................ A61N 1/37217 340/12.5 |
| 2014/0203823 A1 | 7/2014 | Joshi et al. | |
| 2014/0266774 A1* | 9/2014 | Greene .............. A61N 1/37276 340/870.01 |
| 2015/0335285 A1 | 11/2015 | Poon et al. | |
| 2016/0331956 A1 | 11/2016 | Yakovlev et al. | |
| 2018/0028824 A1 | 2/2018 | Pivonka et al. | |
| 2019/0009097 A1 | 1/2019 | Hartley et al. | |
| 2019/0151659 A1 | 5/2019 | Mishra et al. | |
| 2020/0139138 A1 | 5/2020 | Sit et al. | |
| 2020/0222000 A1 | 7/2020 | Poon et al. | |
| 2020/0398058 A1 | 12/2020 | Pivonka et al. | |
| 2021/0196957 A1 | 7/2021 | Yakolev et al. | |
| 2021/0330981 A1 | 10/2021 | Mishra et al. | |

FOREIGN PATENT DOCUMENTS

| | | |
|---|---|---|
| WO | WO-2015139053 A1 | 9/2015 |
| WO | WO-2015196164 | 12/2015 |
| WO | WO-2016127130 A1 | 8/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018126062 A1 | 7/2018 |
| WO | WO-2018156953 A1 | 8/2018 |
| WO | WO-2018208992 A1 | 11/2018 |
| WO | WO-2021003439 | 1/2021 |
| WO | WO-2021067873 | 4/2021 |
| WO | WO-2021/133947 | 7/2021 |

OTHER PUBLICATIONS

U.S. Appl. No. 15/264,864 Office Action dated Oct. 1, 2018.
European Search Report dated Oct. 12, 2017 for European Patent Application No. 15761577.4.
International search report and written opinion dated Jun. 24, 2015 for PCT/US2015/020808.
Office Action dated Oct. 20, 2017 for U.S. Appl. No. 15/264,864.

* cited by examiner

METHOD AND APPARATUS FOR VERSATILE MINIMALLY INVASIVE NEUROMODULATORS

CROSS-REFERENCE TO RELATED APPLICATIONS

This application is a continuation of U.S. patent application Ser. No. 15/264,864, filed Sep. 14, 2016, now U.S. Pat. No. 10,238,872, which is a continuation of PCT Application No. PCT/US2015/020808, filed Mar. 16, 2015, which claims the benefit of U.S. Provisional Application Ser. No. 61/953, 702, filed Mar. 14, 2014, the entirety of which are incorporated herein by reference.

This application is related to: International PCT Application Serial Number PCT/US2014/043023, titled "Method and Apparatus for Minimally Invasive Implantable Modulators", filed Jun. 18, 2014; International PCT Application Serial Number PCT/US2013/067882, titled "Wireless Implantable Sensing Devices", filed Oct. 31, 2013; U.S. Provisional Application Ser. No. 62/015,392, titled "Method and Apparatus for Neuromodulation Treatments of Pain and Other Conditions", filed Jun. 21, 2014; U.S. Provisional Application Ser. No. 62/530,085, titled "Method and Apparatus for Operation with Minimally Invasive Neuromodulators" filed Sep. 19, 2014; U.S. Provisional Application Ser. No. 62/077,181, titled "Method and Apparatus for Implantable Neuromodulation Systems", filed Nov. 8, 2014; and U.S. Provisional Application Ser. No. 62/112,858, titled "Medical Apparatus including an Implantable System and an External System", filed Feb. 6, 2015; the content of each of which is incorporated herein by reference in its entirety.

TECHNICAL FIELD

The embodiments disclosed herein relate generally to apparatus, systems, devices and methods for monitoring, treating and/or diagnosing patients, particularly for neuromodulating tissue.

BACKGROUND

Implantable devices that perform neuromodulation treatments are known. Most use large devices with batteries and long leads to electrically stimulate nerves inside the body. These devices require invasive implantation, which are very costly. They also require periodic battery replacement, which requires additional surgery. The large sizes of these devices and their high costs have prevented their use in a variety of applications that have demonstrated effective neurostimulation treatments.

Nerve stimulation treatments have shown increasing promise recently, showing potential in the treatment of many chronic diseases including drug-resistant hypertension, motility disorders in the intestinal system, metabolic disorders arising from diabetes and obesity, and chronic pain conditions among others. Many of these treatments have not been developed effectively because of the lack of miniaturization and power efficiency, in addition to other factors. Wirelessly powered systems with communication are desirable because they can be miniaturized and have no need for battery replacements. However, wireless systems have an even more restrictive power budget.

There have also been several attempts at developing miniature wireless implantable, neurostimulators, including the device described in U.S. Pat. No. 5,193,539. This device receives power wirelessly, configures stimulation, and performs electrical stimulation in a needle injectible form factor. However, the systems in place for power delivery are highly sensitive to placement and alignment, and offer limited bandwidth for data communications. The receiver operates at MHz frequencies through an inductive link, requiring multiple coils and ferrite cores. More recently, new neurostimulation devices have transitioned to operation at higher frequencies, though these devices presently rely on dipole antennas and struggle with data transfer because of challenges with high-frequency operation. Furthermore, these devices provide stimulation from directly rectifying the power waveform, reducing the precision of control and introducing additional complexity and overhead in the overall system. These systems also have limitations in the duration of pulses that can be delivered, and long pulses can be necessary to induce therapeutic effects for many applications, including gastric stimulation. These systems also rely on instantaneously received power to stimulate excitable tissue and do not aggregate received energy for use in therapy. Additionally, these systems do not provide for a way to use larger non-dipole antennas.

SUMMARY

According to one aspect of the present inventive concepts, a medical apparatus for a patient comprises an external system configured to transmit one or more transmission signals, each transmission signal comprising at least power or data. The apparatus further comprises an implantable system configured to receive the one or more transmission signals from the external system, and the external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and an external controller configured to control the external transmitter. The implantable system comprises a first implantable device comprising: at least one implantable antenna configured to receive the first transmission signal from the first external device; an implantable receiver configured to receive the first transmission signal from the at least one implantable antenna; at least one implantable functional element configured to interface with the patient; an implantable controller configured to control the at least one implantable functional element; an implantable energy storage assembly configured to provide power to an element selected from the group consisting of: the at least one implantable functional element; the implantable controller; the implantable receiver; and combinations thereof; and an implantable housing surrounding at least the implantable controller and the implantable receiver. The medical apparatus is configured to neuromodulate tissue and/or record patient information.

In some embodiments, the apparatus is configured to provide a treatment selected from the group consisting of: medically refractory angina; a movement disorder; pain treatment; cancer pain treatment; chronic critical limb ischemia; complex regional pain syndrome; deep brain stimulation; medically refractory epilepsy; failed back surgery syndrome; fecal constipation; fecal incontinence; urinary incontinence; a urologic disorder; a gastric disorder; GERD; chronic indigestion; gastroparesis; obesity; diabetes; medically refractory headaches; migraine treatment; neuropathy;

neuropathic pain; peripheral neuropathy; pelvic floor dysfunction; Parkinson's disease; Spasticity; and combinations thereof.

In some embodiments, the apparatus comprises a brain-computer interface.

In some embodiments, the apparatus is configured to provide hepatic stimulation to treat diabetes.

In some embodiments, the apparatus is configured to at least one of accelerate or slow down food transit through the gastrointestinal tract.

In some embodiments, the apparatus is configured to provide gastric stimulation.

In some embodiments, the apparatus is configured to provide stimulation selected from the group consisting of: spinal cord stimulation; vagus nerve stimulation; gastric stimulation; sacral nerve stimulation; auditory brainstem stimulation; occipital nerve stimulation; peripheral nerve stimulation; and combinations thereof.

In some embodiments, the apparatus is configured to provide asynchronous transfer of data between the external system and the implantable system. The external system can be configured to transmit power and data to the implantable system, and the data can be transmitted to the implantable system by combining a power carrier with a data signal. The external system can transmit data to the implantable system using ASK modulation. The first external device can transmit an ASK modulated signal to the first implantable device, and data can be encoded in the pulse width. The data transmission can be reconfigurable.

In some embodiments, the apparatus is configured to provide configurable transfer of data between the external system and implantable system. The apparatus can be configured to provide configurable transfer of data from the external system to the implantable system. The data transfer can comprise an adjustable parameter selected from the group consisting of: data rate; pulse width; modulation depth; and combinations thereof.

In some embodiments, the medical apparatus further comprises a data confirmation module configured to assess data transfer integrity. The data confirmation module can be configured to confirm one or more of: transferred data; communication protocol; modulation method; device ID; data preamble; parity codes; encrypting; encoding; and combinations thereof. The data confirmation module can be configured to confirm the integrity of information selected from the group consisting of: transferred data; communication protocol; modulation method; device ID; data preamble; parity codes; encrypting; encoding; variable modulating loads; and combinations thereof. The data confirmation module can comprise a function selected from the group consisting of: handshaking protocol; error checking; reverse data transmission; error correction; repetition codes; parity codes; encryption; communication protocol; encoding device ID; preamble; and combinations thereof.

In some embodiments, the apparatus comprises closed-loop feedback configured to adapt performance of the apparatus in real-time. The apparatus can comprise a treatment parameter, and the treatment parameter can be adjusted based on the closed-loop feedback. The treatment parameter can be adjusted based on performance of the first implantable device. The treatment parameter can be adjusted based on a change in a patient parameter.

In some embodiments, the first external device comprises a unique ID.

In some embodiments, the first external device transmits a security signal periodically to the first implantable device. The first implantable device can perform a calibration routine based on the periodic security signal. The apparatus can be configured to enter a warning state if one or more of the following conditions occur: the first implanted device does not reply to the periodic security signal; the first implanted device does not receive the periodic security signal; and combinations thereof.

In some embodiments, the first external device is configured to adjust a stimulation waveform delivered by the first implantable device.

In some embodiments, the medical apparatus further comprises a second implantable device, and the at least one external antenna transmits at least one of power or data to the second implantable device.

In some embodiments, the at least one external antenna comprises multiple external antennas. The multiple external antennas can be positioned in an array.

In some embodiments, the at least one external antenna transmits an amplitude modulated signal to the first implantable device, and the amplitude is modulated by varying a load on the antenna that causes an impedance mismatch. The amplitude can be modulated by varying a load in a network that causes an impedance mismatch prior to amplifying the signal for transmission.

In some embodiments, the external power supply comprises an element selected from the group consisting of: battery; wall power; and combinations thereof. The external power supply can comprise a rechargeable battery. The battery can comprise a replaceable battery.

In some embodiments, the first external device can further comprise an ultrasound energy delivery element configured to transmit ultrasound energy to the first implantable device. The first implantable device can comprise a transducer configured to receive the ultrasound energy transmitted by the first external device and produce electrical energy. The first implantable device transducer can comprise a piezoelectric material.

In some embodiments, the external system further comprises a patient attachment device constructed and arranged to maintain the at least one external antenna in proximity to the at least one implantable antenna. The patient attachment device can comprise a device selected from the group consisting of: belt; adhesive patch; garment; shirt; and combinations thereof.

In some embodiments, the external system further comprises a peripheral device configured to receive information from the first external device. The peripheral device comprises a device selected from the group consisting of: phone; computer; computer network; and combinations thereof.

In some embodiments, the implantable system further comprises a reference comprising a reference selected from the group consisting of: dynamic reference; a bandgap reference voltage; a bandgap reference; average value; and combinations thereof. The first implantable device can comprise at least one envelope detector; and the dynamic reference can comprise an averaging of a received transmission envelope. The at least one implantable antenna can comprise multiple implantable antennas and each implantable antenna can comprise an associated envelope detector.

In some embodiments, the implantable system comprises at least one transmission module configured to transmit data to the external system. The at least one implantable transmission module can comprise at least one transmission antenna. The at least one implantable antenna can comprise the at least one transmission antenna. The at least one implantable antenna can comprise multiple antennas, and each implantable antenna can comprise an associated implantable transmission module. The at least one transmission antenna can comprise the at least one implantable antenna. The transmission module can comprise a transmission antenna. The at least one transmission module can comprise a backscattering link. The first implantable device can further comprise a variable load connected to the at least one implantable antenna, and data is transmitted by varying the load. The load can be varied to adjust one or more of: backscattered signal amplitude and phase; backscattered signal pulse width; data rate; and combinations thereof. The at least one transmission module can comprise an active transmitter. The transmission module can comprise an oscillator. The at least one transmission module can comprise a body conduction-based transmitter. The body conduction-based transmitter can be charge balanced. The body conduction-based transmitter can comprise code domain multiple access encoding.

In some embodiments, the first implantable device comprises a unique ID. The first external device can be configured to transmit signals to the first implantable device, and the transmitted signal comprises the unique ID.

In some embodiments, the medical apparatus further comprises a second implantable device. The first implantable device can comprise a first unique ID and the second implantable device can comprise a second unique ID. The first external device can be configured to control the first implantable device and the second implantable device independently. The external system can further comprise a second external device, and the external system can be configured to control the first implantable device and the second implantable device independently. The first implantable device can comprise a first received power level, and the second implantable device can comprise a second received power level different than the first received power level. The first implantable device can comprise a first data rate, and the second implantable device can comprise a second data rate different than the first data rate. The second implantable device can comprise an energy storage assembly, and the first implantable device energy storage assembly can comprise a first capacity, and the second implantable device energy storage assembly can comprise a second capacity different than the first capacity. The second implantable device can comprise at least one antenna, and the first implantable device at least one antenna can comprise a first size, and the second implantable device at least one antenna can comprise a second size different than the first size. The first implantable device can comprise a first lead, and the second implantable device can comprise a second lead different than the first lead. The first lead and second lead can comprise different lengths. The first lead and second lead can comprise different configurations of functional elements. The second implantable device can comprise at least one functional element, and the first implantable device at least one functional element can comprise a first set of functional elements, and the second implantable device at least one functional element can comprise a second set of functional elements different than the first set of functional elements.

In some embodiments, the first implantable device comprises at least one operational parameter adjustable by the first external device.

In some embodiments, the at least one implantable antenna is configured to be positioned closer to the patient's skin than the at least one implantable functional element. The at least one implantable antenna can be positioned within the implantable housing.

In some embodiments, the first implantable device comprises a second implantable housing, and the at least one implantable antenna can be positioned within the second implantable housing. The medical apparatus can further comprise a tether between the first implantable housing and the second implantable housing.

In some embodiments, the at least one implantable antenna comprises an antenna selected from the group consisting of: single turn loop antenna; multi-turn loop antenna; electric dipole antenna; magnetic dipole antenna; 3D coil antenna; patch antenna; inductively loaded antenna; capacitively loaded antenna; co-planar spiral antenna; multilayered loop antenna; and combinations thereof.

In some embodiments, the first implantable device comprises a substrate, and the at least one implantable antenna is positioned on the substrate. The substrate can comprise a material selected from the group consisting of: FR4; Rogers material; flexible PCB material; and combinations thereof.

In some embodiments, the medical apparatus further comprises an adjustable inductive load connected to the at least one implantable antenna, the adjustable inductive load configured to be varied to transmit data to the external system.

In some embodiments, the medical apparatus further comprises an adjustable capacitive load connected to the at least one implantable antenna, the adjustable capacitive load configured to be varied to transmit data to the external system.

In some embodiments, the at least one implantable antenna comprises multiple implantable antennas. Each of the multiple antennas can comprise and be connected to an associated power and data receiving module and an associated data transmitting module. The multiple antennas can comprise at least two orthogonally oriented antennas. The first implantable device can combine energy received from at least two implantable antennas. The first implantable device can be configured to select a single antenna to receive power from the first external device based on strength of transmissions received by each of the multiple implantable antennas. The first implantable device can be configured to rectify energy received from the multiple implantable antennas and subsequently combine the energy received.

In some embodiments, the at least one implantable functional element comprises multiple functional elements.

In some embodiments, the at least one implantable functional element comprises at least one electrode.

In some embodiments, the at least one implantable functional element comprises at least one sensor and at least one energy delivery element. The at least one functional element can comprise an electrode configured to sense electrical activity and deliver electrical energy to tissue.

In some embodiments, the at least one functional element comprises one or more functional elements selected from the group consisting of: sensor; transducer; energy delivery element; and combinations thereof. The at least one functional element can comprise an energy delivery element selected from the group consisting of: electrode; electrical energy delivery element; light energy delivery element; sound energy delivery element; mechanical energy delivery element; agent delivery element; and combinations thereof.

In some embodiments, the medical apparatus further comprises a delivery tool, and the at least one functional element is configured to be delivered through the delivery tool. The delivery tool can comprise a tool selected from the group consisting of: needle; endoscope; laparoscope; and combinations thereof.

In some embodiments, the at least one functional element comprises a coating.

In some embodiments, the at least one functional element is configured to be secured to tissue.

In some embodiments, the at least one functional element comprises a barbed end configured to engage with tissue.

In some embodiments, the implantable controller comprises a pulse generator configured to deliver stimulation energy to the at least one functional element. The stimulation energy can comprise electrical energy. The at least one functional element can comprise multiple electrodes. The pulse generator can comprise an adjustable pulse generator. The pulse generator can be configured to be adjusted via data transmitted by the first external device. The pulse generator can be configured to be adjusted via digital data transmitted by the first external device. The pulse generator can be configured to produce stimulation energy with a frequency between 0.1 Hz and 100 KHz. The pulse generator can be configured to provide voltage-controlled stimulation energy. The pulse generator can be configured to provide current-controlled stimulation energy. The implantable controller can further comprise a sensing resistor configured to measure current delivered through the at least one functional element, and the delivered current can be controlled by a digital-to-analog converter. The pulse generator can comprise a digital sensing element configured to sense delivered stimulation energy. The digital sensing element can comprise an analog-to-digital converter. The pulse generator can comprise an analog sensing element configured to sense delivered stimulation energy. The analog sensing element can comprise an error amplifier configured to provide analog feedback of delivered stimulation energy.

In some embodiments, the implantable controller comprises a charge balance module. The charge balance module can be configured to provide passive charge balancing. The passive charge balance module can comprise AC-coupling capacitors. The charge balance module can be configured to provide active charge balancing. The charge balance module can be configured to monitor and control a stimulation parameter selected from the group consisting of: amplitude; polarity; timing information; and combinations thereof. The charge balance module can comprise analog control. The charge balance module can comprise digital control. The implantable controller can further comprise a series resistor, and the charge balance module can be configured to balance charge based on the voltage across the series resistor. The implantable controller can further comprise a voltage monitor, and the charge balance module can be configured to balance charge based on a signal provided by the voltage monitor. The charge balance module can be configured to provide active charge balancing and the residual DC offset can be filtered by passive charge balancing.

In some embodiments, the implantable controller comprises stacked transistors. The stacked transistors can be configured to electrically connect to a voltage of at least 2V, at least 5V or at least 10V.

In some embodiments, the implantable controller is configured to deliver stimulation energy to the at least one functional element and to modify the polarity of the stimulation energy delivered.

In some embodiments, the implantable controller is configured to electrically disconnect from the at least one functional element.

In some embodiments, the implantable controller is configured to transition the at least one functional element from delivering energy to sensing a patient parameter.

In some embodiments, the implantable controller is configured to adjust an amount of energy delivered by the at least one functional element to tissue.

In some embodiments, the implantable controller is configured to sense at least one of a patient parameter or a first implantable device parameter, based on a signal provided by the at least one functional element, and produce sensed data. The at least one functional element can comprise multiple functional elements. The sensed data can comprise data selected from the group consisting of: neural activity; action potentials; muscular activity; biological activity; chemical activity; biochemical activity; physiological activity; pressure; oxygen level; light; pH; impedance; impedance between the at least one functional element and tissue; radioactivity; and combinations thereof. The sensed data can comprise impedance data related to the impedance between the at least one functional element and tissue. The impedance data can be collected by monitoring a parameter selected from the group consisting of: voltage; voltage amplitude; voltage phase; current; current amplitude; current phase; and combinations thereof. The implantable controller can be configured to deliver stimulation energy to the at least one functional element based on the sensed impedance. The sensed data can comprise a first implantable device parameter. The implantable controller can adjust sensing of a patient parameter based on the sensed first implantable device parameter. The first implantable device can be configured to deliver stimulation energy to tissue, and the implantable controller can adjust the delivery of the stimulation energy based on the sensed first implantable device parameter. The implantable controller can comprise a tunable analog front end configured to adjust the sensing of the at least one patient parameter or first implantable device parameter. The tunable analog front end can be configured to adjust an analog front end parameter selected from the group consisting of: gain; low pass cutoff frequency; high pass cutoff frequency; sampling resolution; sampling frequency; and combinations thereof. The tunable analog front end can be configured to be adjusted by the first external device. At least a portion of the tunable analog front end can be configured to be turned off. The tunable analog front end can be configured to perform at least one of asynchronous sampling or event-driving sampling of a signal recorded by the at least one functional element. The implantable controller can comprise an implantable transmitter configured to send the sensed data to the first external device. The implantable transmitter can send an analog representation of the sensed data. The implantable transmitter can send a digital representation of the sensed data. The implantable transmitter can directly modulate a transmitted signal with an analog representation of the sensed data. The first implantable device can transmit the sensed data to the first external device, and the first external device can modify the operation of the first implantable device based on the transmitted sensed data. The first external device can processes the transmitted sensed data and can modify operation of the first implantable device based on the processed transmitted sensed data. The implantable controller can process the sensed data. The first implantable device operation can be modified by the processed sensed data.

In some embodiments, the medical apparatus further comprises an adjustable load connected to the at least one implantable antenna, and the load is adjusted to regulate the amount of energy delivered to the implantable energy storage assembly. The regulated amount of energy can be relatively constant.

In some embodiments, the medical apparatus further comprises an adjustable DC-DC converter, and the adjustable DC-DC converter can comprise parameters that are adjusted to increase efficiency of energy delivery to the implantable energy storage assembly. The adjustable parameters of DC-DC converter can be selected from the group consisting of: switching frequency; conversion ratio; duty cycle; and combinations thereof.

In some embodiments, the implantable energy storage assembly comprises a battery. The battery can comprise a rechargeable battery.

In some embodiments, the implantable energy storage assembly comprises a capacitor.

In some embodiments, the implantable energy storage assembly is configured to store energy at a voltage of at least 5V. The implantable energy storage assembly can be configured to store energy at a voltage of at least 10V.

In some embodiments, the first implantable device further comprises a flexible interconnect connected to the implantable housing. The first implantable device can further comprise a second implantable housing, and the flexible interconnect can be further connected to the second implantable housing. The at least one implantable antenna can be positioned in the second implantable housing. The flexible interconnect can comprise at least one of an active component or a passive component. The at least one of an active or passive component can comprise one or more components selected from the group consisting of: AC-coupling capacitor; bypass capacitor; charge balance capacitor; energy storage element; energy storage capacitor; RF choke; DC-zeroing resistor; and combinations thereof.

In some embodiments, the first implantable device further comprises a matching network. The matching network can comprise a tunable matching network. The matching network can comprise a network selected from the group consisting of: digitally controllable network; analog controllable network; and combinations thereof. The matching network can be configured to be tuned via feedforward tuning. The matching network can be configured to be tuned via feedback-based tuning. The first external device can be configured to transmit feedback data for the feedback-based tuning. The matching network can comprise an adaptive matching network.

In some embodiments, the at least one implantable antenna is connected to a component with an input capacitance such that the at least one implantable antenna forms a resonant circuit.

In some embodiments, the first implantable device further comprises an integrated circuit. The integrated circuit can comprise an element selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; implantable energy storage assembly interface; memory register; timing circuit; power-on-reset circuit; calibration circuit; memory, timing and delay circuit; and combinations thereof.

In some embodiments, the first implantable device further comprises a power management assembly. The power management assembly can comprise an adaptive loading element. The power management assembly can further comprise a rectifier, and loading can be determined by monitoring at least one of the output voltage or current of the rectifier. The power management assembly can comprise a rectifier configured to produce a first voltage, a DC-DC converter configured to produce a second voltage different from the first voltage, and the second voltage is provided to the implantable energy storage assembly. The power management assembly can comprise a multi-stage rectifier, and a first stage of the multi-stage rectifier drives a DC-DC conversion. The power management assembly can comprise a single stage rectifier that produces an output, and a DC-DC converter that receives the output from the single stage rectifier. The power management assembly can comprise impedance DC-DC converter comprising an input impedance, and a rectifier configured to produce an output voltage and a current, and the DC-DC converter can be configured to control at least one of the power management system or the DC-DC converter input impedance by monitoring and controlling the output voltage and the current of the rectifier. The power management assembly can comprise a low-power bandgap reference. The power management assembly can be configured to regulate multiple outputs, and the multiple outputs comprise different voltages. The at least one implantable antenna can comprise multiple antennas, each comprising a rectifier.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

DETAILED DESCRIPTION OF THE DRAWINGS

Figure 1:
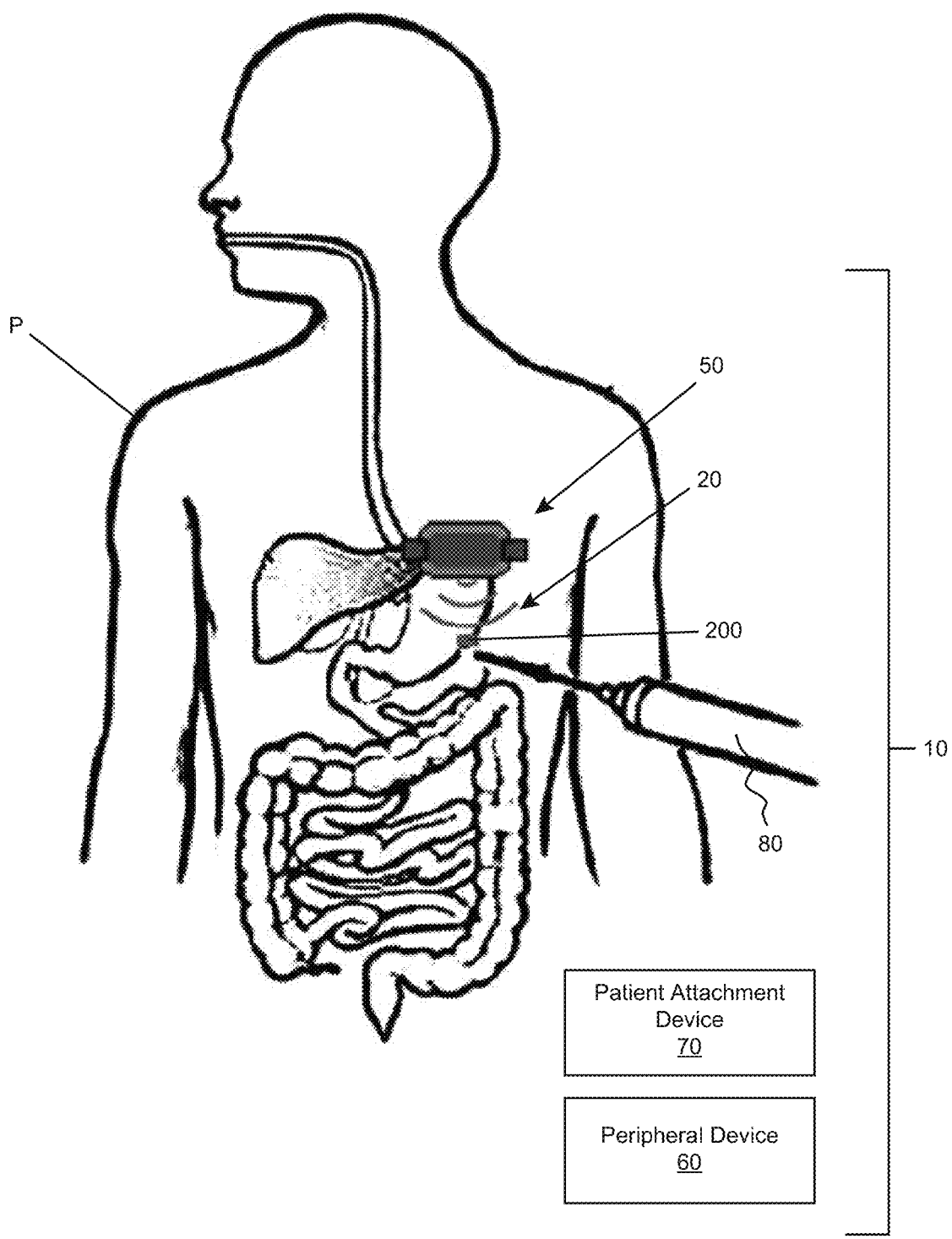
FIG. 1 is a schematic anatomical view of a medical apparatus comprising an implantable system configured for minimally invasive implantation and an external system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such light (e.g. a transducer comprising a light emitting diode or light bulb), sound (e.g. a transducer comprising a piezoelectric material configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezoelectric material); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include a signal transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent from a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts relate to apparatus, systems, devices and methods including minimally invasive devices capable of activation and suppression of tissue or cellular activity and/or sensing with versatility for operation in a wide variety of applications. These apparatus are effective for both chronic and acute treatments, and include devices that can withstand long-term implantation and use under various environments. The apparatus comprise an external system comprising one or more devices positioned outside the patient's body ("external devices") and an implantable system comprising one or more devices positioned at least partially within the patient ("implantable devices".) The implantable devices are capable of producing custom waveforms for stimulation that can be tailored to the treatment and to the specific patient, which can include a closed-loop feedback system that adapts in real-time based on sensed patient or other information. The implantable devices can be capable of one-way or two-way high-speed communication with one or more external devices. The implantable devices use novel configurations of energy delivery, energy management, communications, activation and suppression of physiological activity as will be described herein. There is also a discussion of applications of these apparatus, systems, devices and methods, and potential variations to accommodate different uses.

The present inventive concepts provide apparatus, systems, devices and methods including minimally invasive neuromodulators and sensors using new techniques to improve efficiency, safety and treatment efficacy. The implantable devices can be miniaturized to mm and sub-mm scales depending on the needs of the application. The implantable devices can be packaged in a needle injectible system or with other types of non-invasive or minimally invasive placement tools, including endoscopes or laparoscopic delivery tools. In some cases, multiple implantable devices will operate together to neuromodulate tissue or record information. In some embodiments, an implantable device comprises an implantable antenna configured to collect power that is tethered to one or more functional elements configured to deliver energy to tissue, sense activity of tissue, and/or sense apparatus operational or other parameters, including implantable device and/or external device operational parameters. In these embodiments, the one or more functional elements or other components of the implantable device (e.g. stimulation or sensing control circuitry) can be implanted at a deeper location than the implantable antenna, such that an external antenna transmitting power can be positioned in relatively close proximity to the implantable antenna (e.g. to increase power transfer efficiency). Treatment parameters (e.g. stimulation level, tissue being stimulated, and the like) can be controlled remotely via one or more external devices of the external system and adapted based on performance or changes in one or more conditions (e.g. one or more apparatus conditions and/or patient conditions). The external system can be controlled by a doctor, other health-care provider, the patient, or some combination of these depending on the intended use.

The implantable device can receive power from an external transmitter of an external device via either electromagnetic coupling or through a mechanical energy transfer, such as a transmission of ultrasound energy which is converted to electrical energy (e.g. by a piezoelectric material of the implanted device). The implantable device can operate with a variety of antennas or receivers (e.g. energy-converting transducers) of different sizes. The antenna or receiver area can be proportional to the received power, allowing for flexibility in the design for a specific application based on the power requirements. Power is collected and stored in the implantable device(s) with energy storage elements such as capacitors or in some cases a small battery. The collected energy is efficiently managed and delivered for precise stimulation while also powering all the on board circuitry (e.g. electrically powered components), which can include an radiofrequency (RF) front end, a communication circuit, a digital assembly, one or more functional elements such as electrodes or sensors; an electrode interface, a sensor interface, and other components. This powering configuration can operate with multiple components and assemblies simultaneously with a minimal change in performance, including operation with multiple implantable devices that are independently configured (e.g. multiple implantable devices that receive similar or different power levels from one or more external devices).

High-speed, efficient communication from one or more external devices of the external system to one or more implantable devices of the implantable system can be accomplished by combining data information into the transmitted power signal. This combination is non-trivial, especially at high frequencies, because most data modulation methods have a significant effect on power transfer, and using a separate communication system can result in large interference. Asynchronous data transmission methods can dramatically reduce overhead, and power transfer can remain uninterrupted by employing methods that minimally modulate the amplitude of the power transmission. These data transfer configurations can also operate with multiple implantable devices simultaneously by assigning each implantable device a specific address or other unique ID.

The stimulation waveforms delivered by each implantable device are controlled digitally by a pulse generator of the implantable device that uses energy stored in the implantable device that was received through the power transfer system from one or more external devices. The pulse generator can adjust amplitude, timing and frequency, pulse duration, duty cycle, and/or polarity to precisely control the stimulation waveform delivered by one or more functional elements (e.g. electrodes or other energy delivery element) of the implantable device, to elicit the desired treatment. This configurability of the pulse generator enables variable control of the waveform and/or pulse shape. A digital assembly, a controller, of the implantable device performs the configuration of the stimulation parameters and the pulse generator from data transferred by the external system. This controller also controls operations on the remainder of the implantable device as well, for example, configuration of the communication and/or power management assemblies.

The implantable device can include both an electrode interface for delivering electrical energy to tissue and a sensor interface for recording patient or other information from one or more sensors. Sensors can record patient information such as patient physiologic information or patient environment information. Alternatively or additionally, sensors can record implantable device information, such as implantable device temperature, current, voltage, flow rate (e.g. flow rate of an agent being delivered by the implantable device), or other implantable device operational parameter. The electrodes or other functional elements of each implantable device can include one or more coatings (e.g. depending on the use and the tissue of interest). The functional elements can each be placed and fixed in position with a variety of techniques, such as suturing or by engaging an anchoring component (e.g. a barbed end) of the functional element. The functional elements can comprise one or more sensors including transducers or other sensors that collect physiological, electrical, chemical, or mechanical information that can be used to adapt treatments through a feedback loop, diagnose a patient, and/or simply monitor and report patient or apparatus parameter information.

The external system can include one or more external transmitters to transfer either electromagnetic or mechanical energy to one or more implantable devices. External transmitters can also send and/or receive data from each implantable device to configure it, adapt the treatment, and/or to receive diagnostic or other information from sensors of the implantable device. The external system can be operated by a doctor and/or patient depending on the intended use of the device. The apparatus of the present inventive concepts may include one or more patient attachment devices, such as a patch (e.g. an adhesive patch), a belt, a garment (e.g. a shirt), used to maintain one or more external antennas proximate one or more implanted implantable devices. The external devices can be powered by batteries (e.g. replaceable and/or rechargeable batteries) and/or be plugged into a wall outlet depending on where and how treatment is delivered and other factors. In some embodiments, one or more external device can also communicate with computers and/or smart phones to relay information about the operation of the apparatus and to allow for reconfiguration of the apparatus.

The apparatus of the present inventive concepts can be used in a diverse set of applications including gastrointestinal disorders, hypertension, pain management, deep brain stimulation (DBS), auditory conditions, physical therapy, electro-acupuncture, veterinary, reproductive, and any other applications where neuromodulation and/or sensing provides beneficial therapy and/or diagnostics. These applications are not limited to medical applications, and may include consumer applications in which the implantable device described herein is not implanted and performs monitoring or some form external neuromodulation.

Medical apparatus including one or more implantable devices are limited in their performance by a power budget, which restricts both miniaturization and functionality of each implantable device. Implantable devices configured to neuromodulate tissue can require significant power to provide therapy because of the relatively high voltage and current requirements needed to cause effective stimulation. For fully wireless systems, the power limitation is typically a significant design constraint and limits the performance of the apparatus.

Referring now to FIG. 1, a medical apparatus for a patient is illustrated, consistent with the present inventive concepts. Apparatus 10 comprises external system 50 and implantable system 20. Implantable system 20 can comprise one or more implantable devices 200. Apparatus 10 can comprise a neuromodulation apparatus or other apparatus configured to modulate or otherwise stimulate tissue. Alternatively or additionally, apparatus 10 can comprise an apparatus configured to record one or more patient parameters, such as one or more patient physiologic and/or patient environment parameters. Apparatus 10 can be configured to report the patient parameters and/or use patient parameter information to adjust the performance of apparatus 10 (e.g. adjust stimulation in a closed-loop fashion). Apparatus 10 can further comprise tool 80 which can be constructed and arranged to implant one or more implantable devices in a minimally invasive way, such as when tool 80 comprises a needle through which an implantable device 200 can be implanted in the patient P as shown. In some embodiments, tool 80 comprises a needle; a laparoscope or an endoscope. Apparatus 10 can comprise a patient attachment device 70 and/or a peripheral device 60, as shown in FIG. 1 and described herebelow.

External system 50 can be configured to provide power to one or more implantable devices 200. Each implantable device 200 can be configured to comprise millimeter (e.g. 1-10 mm) and sub-millimeter dimensions (e.g. length, width, major axis and/or minor axis dimensions) while offering the flexibility to operate with different "power budgets" (e.g. power consumption rates). Each implantable device 200 can comprise a controller (e.g. controller 250 of FIG. 2) that configures, adjusts or otherwise controls on-board circuitry (e.g. one or more analog, digital or other electronic components) such as a pulse generator (e.g. pulse generator 280 of FIG. 2) that can produce stimulation waveforms (e.g. customized and/or adjustable stimulation waveforms) to accommodate one or more intended treatments. The pulse generator can be configured to control amplitude; timing and frequency; pulse duration; duty cycle and/or polarity of one or more stimulation waveforms delivered by implantable device 200 to tissue. This configurability of the pulse generator allows construction of variable stimulation waveforms and/or pulse shapes. In some embodiments, apparatus 10 comprises at least a first implantable device 200a and a second implantable device 200b, each of which can be configured to receive power and/or data from one or more external devices 500 of external system 50. Each implantable device 200 can comprise a unique ID, such as to ensure proper transmissions from external system 50. Each implantable device 200 can be configured to receive similar or dissimilar transmissions (e.g. similar or different power level or other power transmission parameter and/or similar or different data rates or other data transmission parameter). Each implantable device can comprise a similar or different energy storage assembly 270, such as is described herebelow, such as energy storage assemblies 270 with similar or different capacities. Each implantable device 200 can comprise an implantable antenna 240 (comprising one or more implantable antennas), one or more functional elements 260, one or more leads 265, each described in detail herebelow. Each implantable device 200 can comprise similar or different implantable antennas 240, similar or different quantity and/or configuration of functional elements 260, similar or different implantable leads 265 (e.g. different lengths or different configuration of functional elements 260 on lead 265), and combinations of one or more of these.

External system 50 can be configured to transmit power and/or data to one or more implantable devices 200 of implantable system 20. External system 50 can comprise one or more external devices, such as external device 500 described herebelow, each configured to transmit power and/or data to one or more implantable devices 200, and/or to receive data from one or more implantable devices 200. External system 50 can comprise a separate communication protocol, such as Bluetooth, used to interface with computers, smart phones, one or more computer networks, and/or other peripheral devices, such as peripheral device 60 shown in FIG. 1.

External system 50 can include a transmitter to transfer electromagnetic and/or mechanical energy to one or more implantable devices 200 of implantable system 20. This transmitter can also send and/or receive data from each implantable device 200, such as to configure the implantable device 200 and/or adapt a treatment being delivered by the implantable device 200. In some embodiments, one or more implantable devices 200 are configured to record patient data, such as to perform a patient diagnostic, as described herebelow. Each implantable device 200 can be constructed and arranged as described herebelow in reference to FIG. 2 and each external system 50 can comprises one or more external devices of similar construction and arrangement to external device 500 described herebelow in reference to FIG. 3. External system 50 can be operated by either a healthcare provider (e.g. a doctor, nurse or other skilled healthcare provider) and/or the patient, depending on the intended use and clinical safety requirements of the device. Apparatus 10 can comprise one or more patient attachment devices, such as patient attachment device 70 shown in FIG. 1, that can be configured to attach of one or more portions of external system 50 to the patient, such as a patch, a belt, or a garment (e.g. a shirt), to name a few. External system 50 can be powered by batteries and/or it can be plugged into wall power depending on where and how treatment is to be delivered. External system 50 can also communicate with a peripheral device, such as peripheral device 60 shown. Peripheral device 60 can comprise a computer (e.g. a desktop computer, a laptop computer, a tablet, and the like); a smart phone; a computer network; and combinations of one or more of these. Peripheral device 60 can receive information about the operation of apparatus 10 and/or to allow for reconfiguration of apparatus 10.

Figure 2:
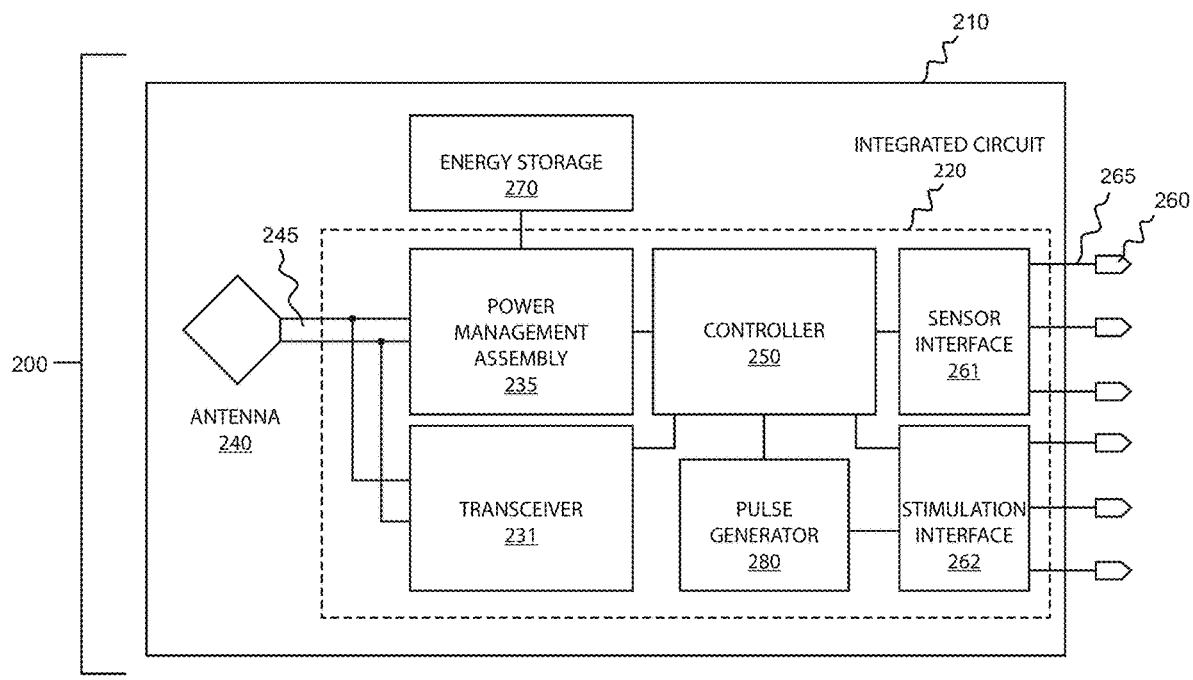
FIG. 2 is a schematic view of an implantable device comprising an integrated circuit, energy storage, and an implantable antenna, consistent with the present inventive concepts.

Referring now to FIG. 2, a schematic view of an implantable device 200 is illustrated, consistent with the present inventive concepts. Implantable device 200 comprises an implantable integrated circuit 220, implantable energy storage assembly 270, implantable antenna 240 and at least one implantable functional element 260. Antenna 240 can comprise one or more implantable antennas. Functional element 260 can comprise one or more implantable sensors or transducers, such as an electrode configured to deliver electrical energy to tissue and/or to record electrical activity of tissue. Energy storage assembly 270 can comprise one or more components selected from the group consisting of: battery; rechargeable battery; capacitor; and combinations of one or more of these. In some embodiments, energy storage assembly 270 is configured to store energy at a voltage of at least 5V, such as at least 10V. Integrated circuit 220 can comprise power management assembly 235, controller 250, sensor interface 261, stimulation interface 262, pulse generator 280 and/or transceiver 231, each of which can be operably connected as shown in FIG. 2. In some embodiments, one or more antennas 240 each have an associated matching network 241, rectifier 232, transceiver 231, and/or boost converter 233, not shown but described herebelow. In some embodiments, with multiple implantable antennas 240, implanted controller 250 is configured to select a transceiver 231 (of a set of transceivers 231) for data receiving and transmitting, such as to select a transceiver 231 which has the strongest coupling with one or more external antennas 540. Integrated circuit 220 and energy storage assembly 270 can be positioned within an implantable housing, housing 210. Housing 210 can comprise multiple parts which are sealed together (e.g. to create a hermetic or other seal configured to prevent contamination from passing through housing 210). In some embodiments, one or more antennas 240 are also positioned within housing 210. Alternatively, one or more antennas 240 are positioned outside of housing 210, such as within a second housing, not shown. One or more functional elements 260 can be positioned within and/or on housing 210. Alternatively, one or more functional elements 260 are positioned on, in and/or within a lead attached to housing 210, lead 265 as shown, such as an implantable lead comprising one or more electrodes. The components within housing 210 are designed, constructed and arranged to allow miniaturization of housing 210 to support minimally invasive implantation, such as implantation through a needle as described hereabove, an endoscope, a laparoscope, or other delivery tool. Antenna 240 receives power and/or data from an external antenna, such as external antenna 540 described herebelow in reference to FIG. 3, which can receive power from batteries and/or a wall outlet. The external antenna is positioned on or near the surface of the patient's skin in close proximity to implantable antenna 240 (e.g. an antenna 240 positioned within housing 210). Antenna 240 can receive power and/or data from one or more external antennas of external system 50.

Figure 3:
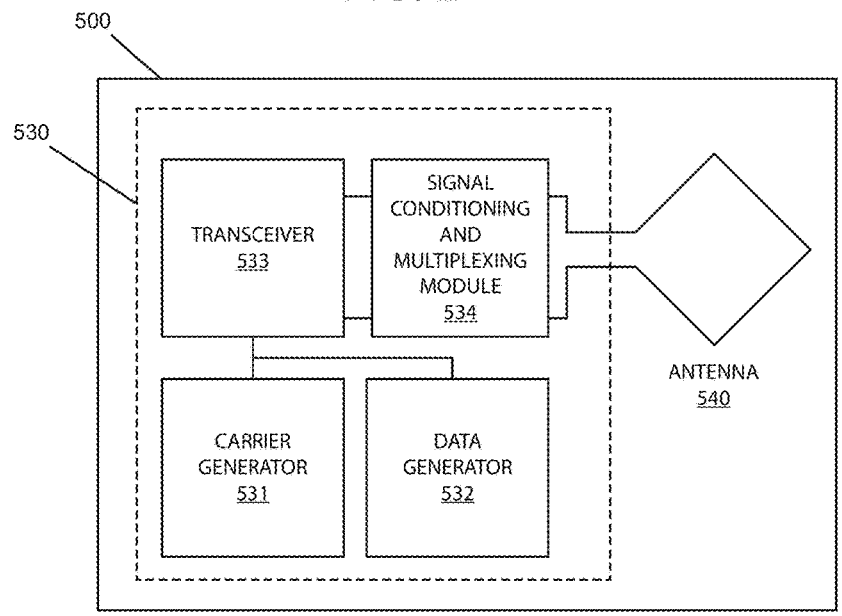
FIG. 3 is a schematic view of an external device comprising an external transmitter and an external antenna, consistent with the present inventive concepts.

Referring additionally to FIG. 3, a schematic view of an external device 500 is illustrated, consistent with the present inventive concepts. External device 500 comprises external transmitter 530 and external antenna 540 (e.g. one or more external antennas). External transmitter 530 can comprise external transceiver 533, signal conditioning and multiplexing module 534, carrier generator 531, and data generator 532. Data can be transferred from external device 500 to one or more implantable devices 200 at speeds up to and exceeding 20 Mbps to accommodate configuration and control of the implantable device 200 as well as real-time treatment adjustments of implantable device 200. Data and power can be transferred by external device 500 to multiple implantable devices 200 (e.g. simultaneously or sequentially), and the high-speed of communication to each implantable device 200 can allow one or more implantable devices 200 to adapt and adjust in real-time. In some embodiments, an implantable device 200 can comprise one or more functional elements 260 configured as sensors, such as to make use of the high-speed communication for internal (e.g. implantable device 200) diagnostics and/or real-time feedback of patient information (e.g. patient physiological or patient environment information), such as to inform the doctor or patient of the functionality of the device and/or to provide patient information feedback to the medical apparatus to adapt the treatment (e.g. in a closed loop fashion).

In some embodiments, implantable antenna 240 comprises one or more implantable antennas positioned outside of housing 210. In these embodiments, the delivery of implantable device 200 to a target site is performed in a way such that one or more functional elements 260 are placed in proximity to a target nerve, muscle, organ, and/or other tissue and implantable antenna 240 is placed close to the tissue surface such that the implantable antenna 240 is in closer proximity to the patient's skin, than housing 210 and/or functional element 260, such as is described herebelow in reference to FIG. 9. Implantable device 200 can comprise a second housing, such as when antenna 240 comprises the second housing which surrounds one or more antennas of antenna 240. Functional elements 260 (e.g. one or more electrodes) can be positioned on housing 210 and/or they can be connected to housing 210 (e.g. electrically and/or otherwise operably connected to one or more components within housing 210) with flexible interconnects or leads (hereinafter "leads", "interconnects" or "conduits"), such as leads 265 shown and/or interconnects 242 described herebelow. Each flexible interconnect and/or lead 265 can include (e.g. surround) one or more passive or active components, such as a component selected from the group consisting of: AC-coupling capacitor; bypass capacitor; charge balance capacitor; energy storage element; energy storage capacitor; RF choke; DC-zeroing resistor; and combinations thereof. Antenna 240 can be positioned within housing 210 and/or it can be positioned outside of housing 210 and connected to housing 210 (e.g. electrically and/or otherwise operably connected to one or more components within housing 210) with one or more leads, leads 245 shown. Leads 245 and/or 265 can be of adjustable length or fixed length. Implantable device 200 can comprise one or more leads configured to attach various components of implantable device 200 together, such as to operably connect (e.g. at least electrically connect) implantable antenna 240 to circuitry within housing 210, and/or to connect one or more functional elements 260 (e.g. one or more electrodes) to the circuitry within housing 210. In some embodiments leads 245, leads 265 and/or flexible interconnects 242 include passive and/or active components (e.g. on, in and/or within each component, such as capacitors and/or inductors as part of a charge balance circuit, matching network, and/or energy storage assembly 270).

In some embodiments, an implantable device 200 is configured for implantation through a needle or other delivery device (e.g. tool 80 described hereabove in reference to FIG. 1), and housing 210 comprises a dimension (e.g. a diameter, width or minor axis dimension) of approximately 2 mm or less (e.g. when housing 210 surrounds energy storage assembly 270 and integrated circuit 220 and/or antenna 240). In some embodiments, antenna 240 is positioned outside of housing 210, and antenna 240 also comprises a dimension (e.g. a diameter, width or minor axis) of approximately 2 mm or less, such as a dimension between 0.3 mm and 2 mm (e.g. when implantable device 200 comprises a second implantable housing surrounding antenna 240). In some embodiments, antenna 240 is positioned outside of housing 210, and is configured to comprise a dimension (e.g. a diameter, width, or minor axis) of approximately 2 mm or less prior to implantation, such as a dimension which expands to a larger dimension after implantation (e.g. an unfoldable or unfurlable antenna 240). In other embodiments, housing 210 comprises a dimension between 2 mm to 20 mm (e.g. when housing 210 surrounds one or more antennas 240). Housing 210 can comprise one or more feedthroughs configured to operably connect antenna 240 and/or functional element 260 to integrated circuit 220 (e.g. when antenna 240 and/or functional element 260 comprise lead 265 configured to pass through the one or more feedthroughs of housing 210), while providing a seal between housing 210 and lead 265, such as to prevent contamination from passing between housing 210 and lead 265. In some embodiments, housing 210 comprises a first end with one or more feedthroughs through which a lead 245 of antenna 240 passes, and a second end with one or more feedthroughs through which a lead 265 of one or more functional elements 260 passes, such as is described herebelow in reference to FIG. 4. Alternatively or additionally, a flexible interconnect 242 as described herein passes through a feedthrough of housing 210 or another housing of implantable device 200 (e.g. in a sealed manner). In some embodiments, implantable device 200 is constructed and arranged as is described herebelow in reference to FIGS. 5, 6, 7 and/or 8.

As described herein, each implantable device 200 implantable antenna 240 (e.g. comprising one or more antennas) can be configured to wirelessly receive power and/or data from one or more external devices 500 via its external antenna 540 (e.g. comprising one or more antennas). Each implantable device 200 can be configured to capture oscillating electromagnetic waves contained in a power signal transmission delivered by one or more external devices 500. The captured electromagnetic waves can be converted into a direct current (DC) signal using rectification circuitry of power management assembly 235, for further use by implantable device 200 (e.g. to charge energy storage assembly 270 and/or to provide energy to antenna 240 and/or one or more components of integrated circuit 220).

As described hereabove, implantable device 200 can comprise one or more sealed housings which contain one or more antennas, integrated circuits, power storage elements (e.g. batteries), passive components, active components, or other components. Implantable device 200 can comprise components configured to provide one or more of: a matching network; DC-DC conversion circuits, rectification and/or other functions. The multiple housings (e.g. housing 210, a housing of antenna 240 and/or a housing of functional elements 260 can be connected via rigid, semi-rigid or flexible interconnects, such as leads, flexible PCB, or wires. The multiple housings can be configured as described herebelow in reference to FIGS. 4, 5, 6, 7 and/or 8.

Antenna 240 can comprise one or more antennas selected from the group consisting of: single loop antennas; multi-turn loop antenna; electric dipole antenna; magnetic dipole antenna; patch antenna; 3-dimensional (3D) antenna; 3D coil antenna; and combinations of one or more of these. In some embodiments, antenna 240 comprises one or more planar antennas implemented on a printed circuit board (PCB) comprising a substrate made of various materials such as FR4, Rogers, and/or a flexible substrate. Antenna 240 can comprise multiple loops that are achieved in a form of a co-planar spiral or a multilayered loop with one or more turns on each layer. Antenna 240 can comprise inductively and/or capacitively loaded antennas, such as to reduce the physical antenna size. Each antenna 240 can comprise and/or otherwise be connected to an associated power and/or data receiving module, and/or a data transmitting module, each as described herein. In some embodiments, antenna 240 comprises one or more antennas as described herebelow in reference to FIGS. 10A-J.

In some embodiments, antenna 240 comprises multiple antennas positioned in orthogonal or other non-planar orientations (e.g. with respect to each other) to ensure that an incoming power transmission is captured regardless of the position or orientation of antennas 240 with respect to the transmitting external antenna 540. Antenna 240 can comprise multiple different antennas, such as two or more antennas as described herein, where each antenna is configured to capture energy in a particular way. For example, antenna 240 can comprise an electric dipole antenna and a magnetic dipole antenna, with the electric dipole antenna configured to primarily capture energy contained in an electric field and the magnetic dipole antenna configured to primarily capture energy contained in a magnetic field. The captured energy by the two antennas of antenna 240 can be used either in combination or by selecting the antenna receiving more energy. In some embodiments, antenna 240 comprises a single loop antenna with a single turn. In these embodiments, antenna 240 can be implemented on a flexible printed circuit substrate with a major axis between 4 mm and 15 mm (e.g. approximately 5 mm) and a minor axis between 1 mm and 10 mm (e.g. approximately 2 mm). This flexible substrate implementation can be configured to allow antenna 240 to be compacted (e.g. rolled up into a cylindrical shape), such as to ease delivery through a lumen of a needle (e.g. a large-bore hypodermic needle) or other implantation tool (e.g. tool 80 of FIG. 1). Antenna 240 can be configured to have a self-resonance frequency above the operating frequency at which a power signal is being transmitted by one or more external devices 500. In this configuration, capacitive loading of the power harvesting circuitry of integrated circuit 220, together with the inductive impedance of antenna 240, form a resonant circuit which resonates at the power carrier frequency (e.g. a frequency between 0.300 GHz and 3 GHz, such as a frequency of approximately 0.434 GHz, 0.915 GHz, 2.45 GHz, or 1.5 GHz). A specific frequency band of operation can be determined based on one or more factors including but not limited to: a regulatory standard; application; the size and/or impedance of one or more antennas 240; and/or a capacitive loading impedance. Also, as described herein, the frequency of a transmission from an external device 500 can be tuned with a matching network of an implantable device 200 to ensure sufficient bandwidth is allowed to accommodate forward communication (i.e. data sent from an external device 500 to an implantable device 200) and reverse communications (e.g. data sent from an implantable device 200 to an external device 500. For example, for operation in the 915 MHz ISM band, a tuning network can be configured to provide a match between antenna 240 and a rectifier of integrated circuit 220, such that return loss is better than −6 dB within the entirety or a portion of the 902 MHz to 928 MHz band.

Antenna 240 can comprise one or more unfoldable and/or expandable antennas, such as are described in International PCT Patent Application Serial Number PCT/US2014/043023, entitled Method and Apparatus for Minimally Invasive Implantable Modulators, the content of which is incorporated herein by reference in its entirety. Antenna 240 comprising one or more unfoldable and/or expandable antennas allow for antennas with large cross-sections, which can receive increased power while still be delivered through a minimally invasive tool (e.g. a needle).

Figure 4:
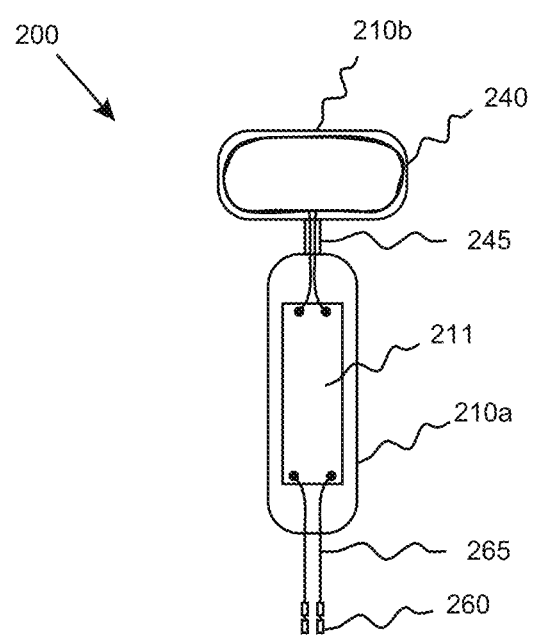
FIG. 4 is a top view of an implantable device comprising an implantable housing and an implantable antenna external to the implantable housing, consistent with the present inventive concepts.

In the embodiment shown in FIG. 4, implantable device 200 comprises implantable housing 210a which surrounds substrate 211. Substrate 211 can include one or more integrated circuits (e.g. integrated circuit 220 described hereabove in reference to FIG. 2), one or more passive components, one or more active components, and/or one or more assemblies. Implantable antenna 240 is positioned in a separate housing, implantable housing 210b as shown. Housing 210b is connected (e.g. electrically connected) to housing 210a via a flexible interconnect as shown. Functional element 260 (e.g. one or more electrodes) is positioned outside of housings 210a and 210b, for example on a flexible lead attached to housing 210a, also as shown.

Figure 5:
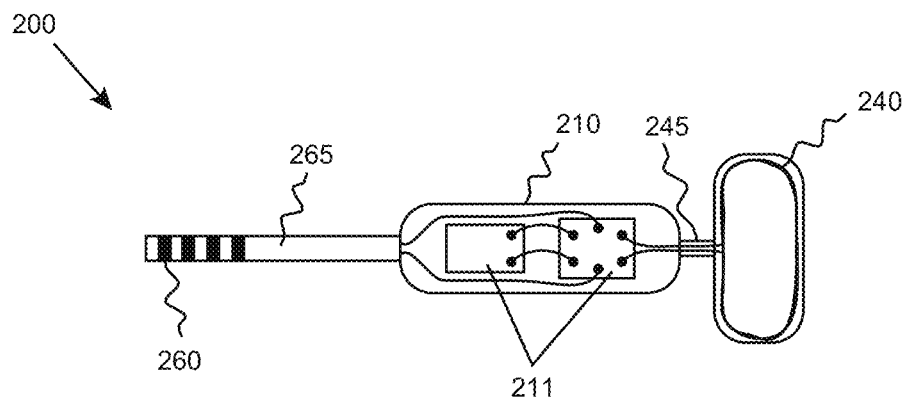
FIG. 5 is a top view of an implantable device comprising an implantable housing, an implantable antenna positioned outside of the housing, and an implantable lead comprising multiple functional elements, consistent with the present inventive concepts.

In the embodiment shown in FIG. 5, implantable device 200 comprises implantable housing 210, implantable antenna 240 positioned outside of housing 210 and connected (e.g. electrically connected) to housing 210 via a flexible interconnect, and implantable functional elements 260 (e.g. one or more electrodes) positioned on lead 265 which attaches to housing 210. Housing 210 surrounds multiple substrates 211, each of which can include one or more integrated circuits (e.g. integrated circuit 220 described hereabove in reference to FIG. 2) and/or other passive components, active components, or assemblies as described herein.

Figure 6:
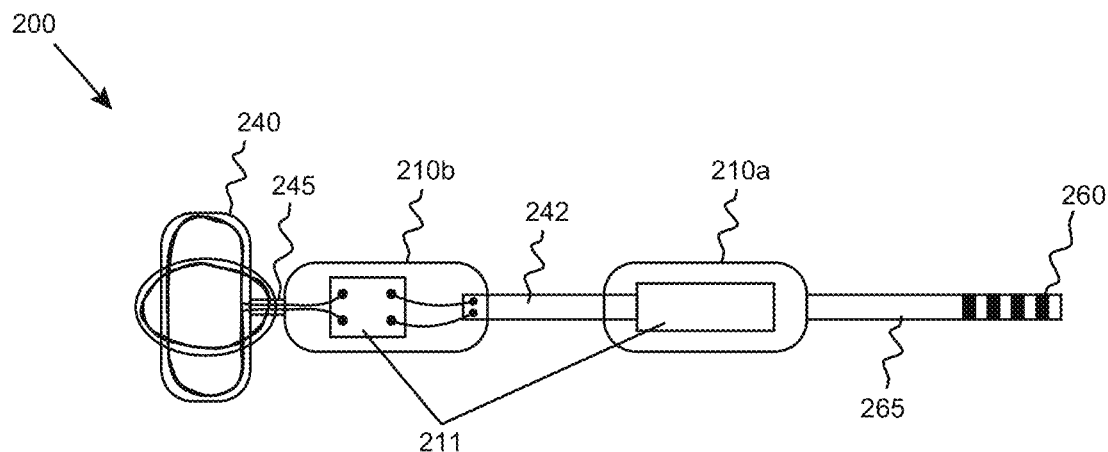
FIG. 6 is a top view of an implantable device comprising two implantable housings, an implantable antenna positioned outside of the two implantable housings, and an implantable lead comprising multiple functional elements, consistent with the present inventive concepts.

In the embodiment shown in FIG. 6, implantable device 200 comprises multiple implantable housings, housings 210a and 210b as shown, and an antenna 240 comprising multiple implantable antennas positioned in different planes (e.g. positioned in two or more orthogonal planes) with respect to each other. Housings 210a and 210b each include a substrate 211 which can include one or more integrated circuits (e.g. integrated circuit 220 described hereabove in reference to FIG. 2) and/or other passive components, active components, or assemblies as described herein. In some embodiments, capacitors that are part of a charge balancing circuit can be housed in a separate housing 210. Housings 210a and 210b can be connected (e.g. electrically connected) via a flexible conduit, such as interconnect 242 shown, which can include one or more electrical wires, optical fibers, fluid transport tubes, and the like.

Figure 7:
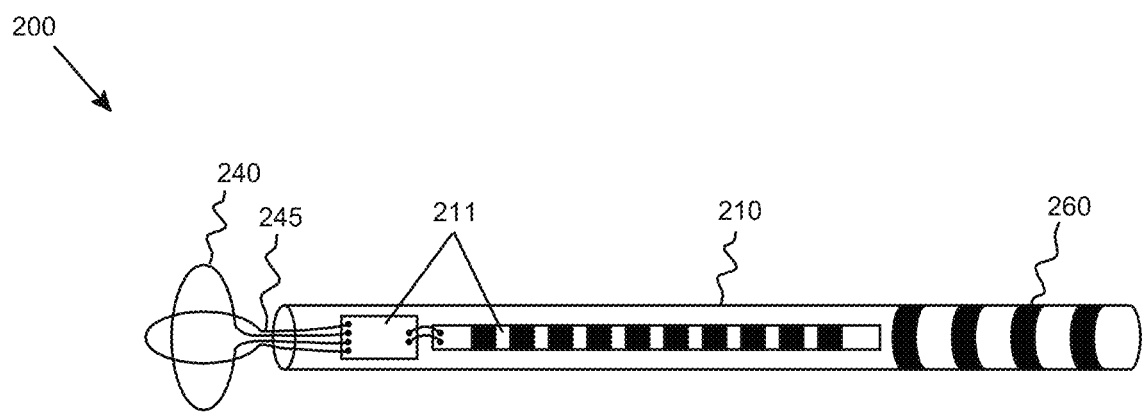
FIG. 7 is a top view of elongate implantable housing, an implantable antenna positioned outside of the implantable housing, and multiple functional elements positioned on the implantable housing, consistent with the present inventive concepts.

In the embodiments of FIG. 7, implantable device 200 comprises housing 210 (e.g. an elongate housing whose length is more than twice as long as its width), functional elements 260 and antenna 240. Antenna 240 can comprise two antennas positioned on different planes (e.g. positioned orthogonal to each other). Functional elements 260 can be positioned on housing 210 as shown. Housing 210 can surround multiple substrates 211, which can each include one or more integrated circuits (e.g. integrated circuit 220 of FIG. 2) and/or other active or passive components as described herein. In some embodiments, an elongate housing is operably attached to a lead 245 and/or a lead 265 as described hereabove, and surrounds one or more substrates 211, such as a substrate 211 that includes passive components that are part of a charge balancing circuit.

Figure 8:
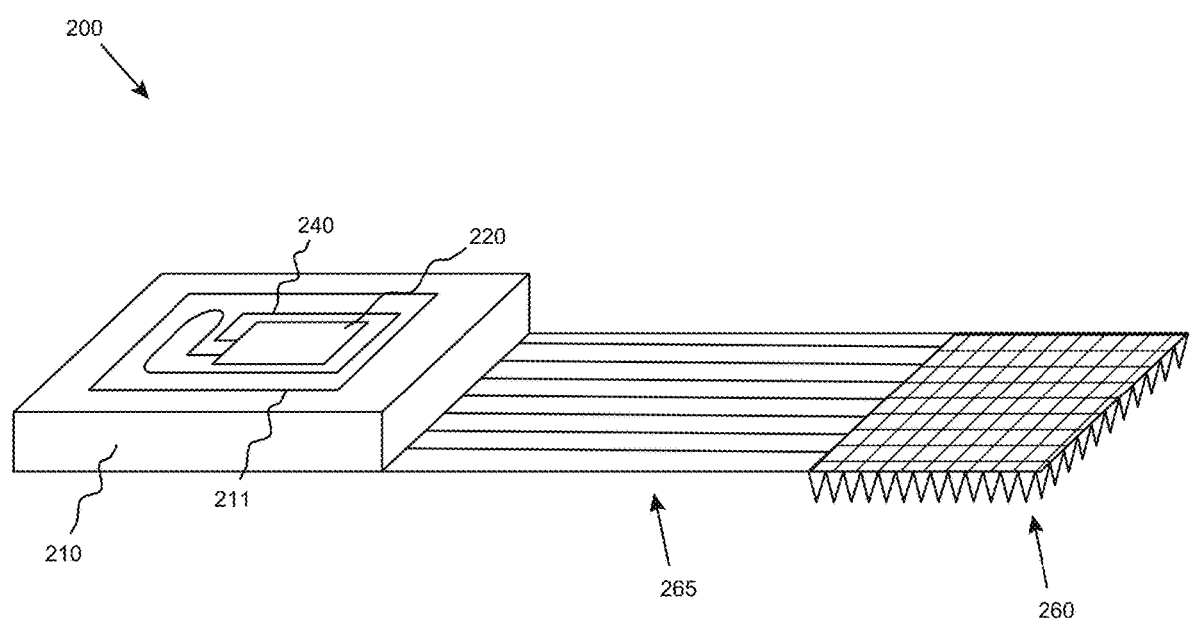
FIG. 8 is a view of an implantable device comprising an implantable antenna surrounding an implantable antenna positioned on a substrate comprising an integrated circuit, and an array of functional elements, consistent with the present inventive concepts.

In the embodiment of FIG. 8, implantable device 200 comprises antenna 240 which is positioned and/or constructed on substrate 211, which is surrounded by implantable housing 210. Substrate 211 can comprise a printed circuit board (PCB), a flexible PCB, or other substrate. Implantable device 200 further comprises functional elements 260 which include an array of functional elements, such as an array of electrodes in a "bed of nails" arrangement as shown. Substrate 211 can include integrated circuit 220 as shown (e.g. of similar construction and arrangement as integrated circuit 220 of FIG. 2) and/or other passive or active components. Functional elements 260 are connected to housing 210 via a flexible interconnect.

Figure 9:
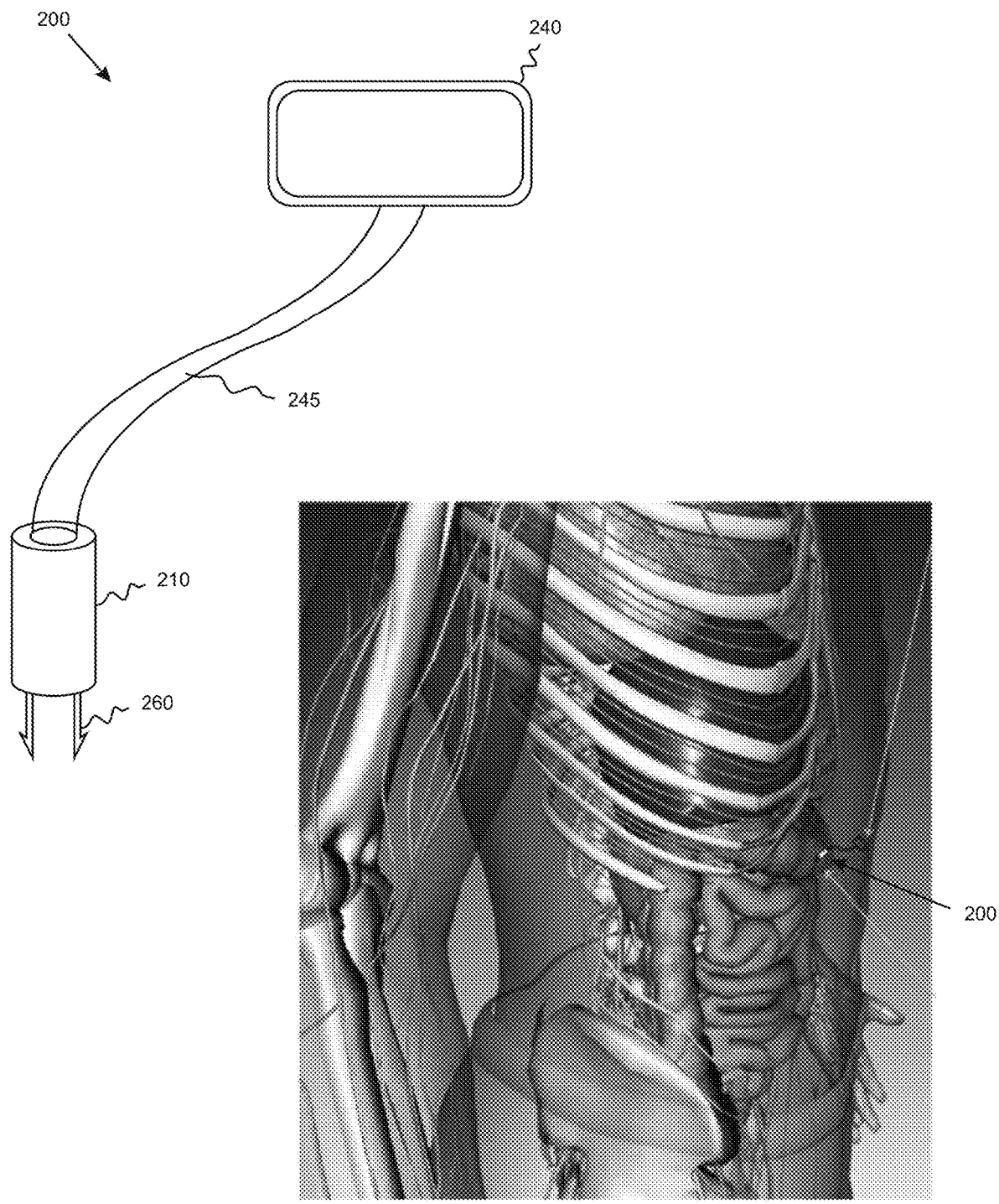
FIG. 9 is a top view and an anatomical view of an implantable device comprising a housing, an implantable antenna positioned outside of the housing, and a functional element comprising barbed members, consistent with the present inventive concepts.

In the embodiment of FIG. 9, implantable device 200 comprises housing 210, implantable antenna 240, and functional elements 260. Functional elements 260 can comprise an anchoring element, such as a harpoon or barbed structure. As shown in the anatomical view of FIG. 9, in some embodiments, housing 210 and/or functional elements 260 can be implanted near the therapy site (e.g. tissue to be stimulated or physiologic data recorded from) while one or more antennas 240 are positioned proximate the surface of skin (e.g. to be in close proximity to an external device 500 antenna 540).

Figure 10A:
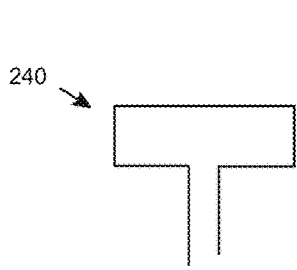
FIGS. 10A-10J are views of various antennas, consistent with the present inventive concepts.
Figure 10B:
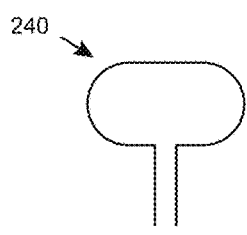
Figure 10C:
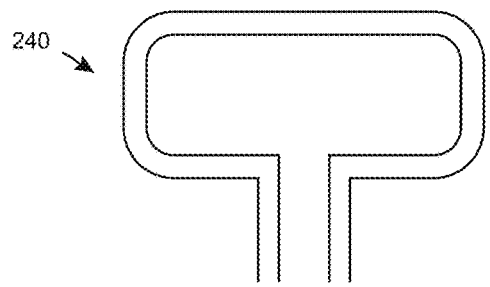
Figure 10D:
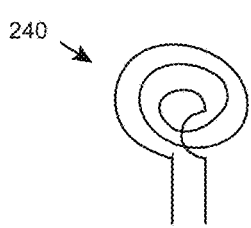
Figure 10E:
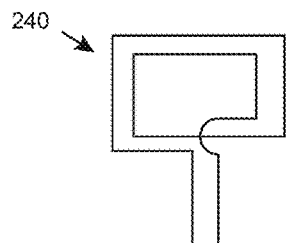
Figure 10F:
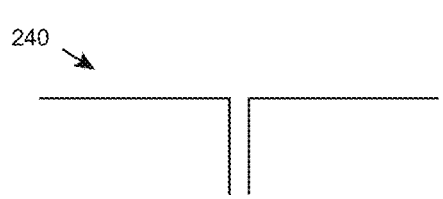
Figure 10G:
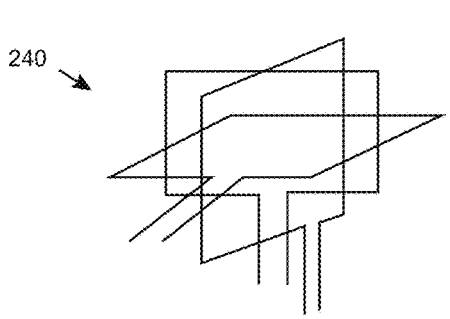
Figure 10H:
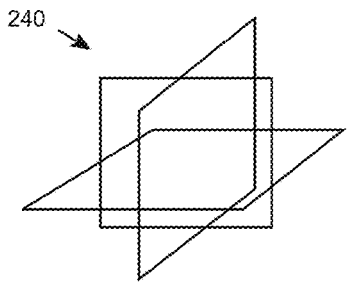
Figure 10I:
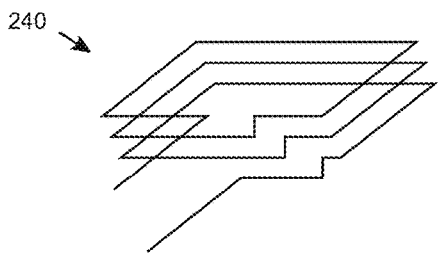
Figure 10J:
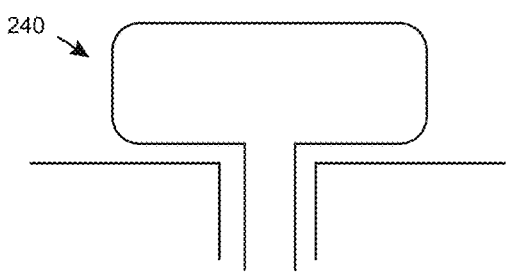

FIGS. 10A-10J illustrate various antenna configurations of implantable antenna 240 of the present inventive concepts. In FIG. 10A, an implantable antenna 240 comprising a square loop geometry antenna is illustrated. In FIG. 10B, an implantable antenna 240 comprising a circular or oval-shaped loop geometry antenna is illustrated. In FIG. 10C, an implantable antenna 240 comprising a foldable substrate is illustrated. In FIG. 10D, an implantable antenna 240 comprising a curved spiral geometry is illustrated. In FIG. 10E, an implantable antenna 240 comprising a rectangular spiral geometry antenna is illustrated. In FIG. 10F, an implantable antenna 240 comprising a dipole antenna is illustrated. In FIG. 10G, an implantable antenna 240 comprising multiple antennas positioned on different planes (e.g. orthogonal planes) is illustrated. In FIG. 10H, an implantable antenna 240 comprising an antenna with orthogonal rectangular conductors is illustrated. In FIG. 10I, an implantable antenna 240 comprises an antenna including a loop with multiple turns is illustrated. In FIG. 10J, an implantable antenna 240 comprising a loop antenna and a dipole antenna is illustrated.

While the antenna configurations of FIGS. 10A-10J have been described as applicable to implantable antenna 240 of the present inventive concepts, each design can be incorporated into external antenna 540 of the present inventive concepts as well.

Implantable device 200 can comprise an impedance matching network operably connecting antenna 240 to power harvesting circuitry of integrated circuit 220, such as to minimize mismatch between antenna 240 impedance and integrated circuit 220 input impedance and/or otherwise improve efficiency. Integrated circuit 220 can comprise the matching network (e.g. on-chip) or a fully or partially off-chip configuration can be implemented. If needed, the off-chip matching network can comprise one or more elements selected from the group consisting of: discrete components, such as surface mount capacitors, inductors and/or transformers; distributed components, such as transmission lines with stubs and/or tapered transmission line; and one or more of combinations of these. The matching network can comprise a variety of topologies, such as L-, T-, Pi- or higher order matching networks, it can be balanced or un-balanced, and/or it can be transformer-based. Some or all of the matching network components can be made tunable or otherwise adjustable, such as to minimize the reflection coefficient between antenna 240 and integrated circuit 220 impedances. For example, in an L-match network implemented using on-chip capacitors, extra capacitors can be added (or removed) in parallel to tune the capacitance by controllably closing switches which are placed in series with the capacitors, allowing for digital control of capacitance included in the matching network. Alternatively, tuning can be accomplished using analog control by implementing tunable capacitors using diodes or variable capacitors, and by controlling their bias voltage. The tuning can be accomplished either in a closed loop or open loop manner. Closed loop control can be accomplished either completely on-chip or by communicating information to the external device 500, which can then send information to an implantable device 200 to tune the matching network.

Figure 11:
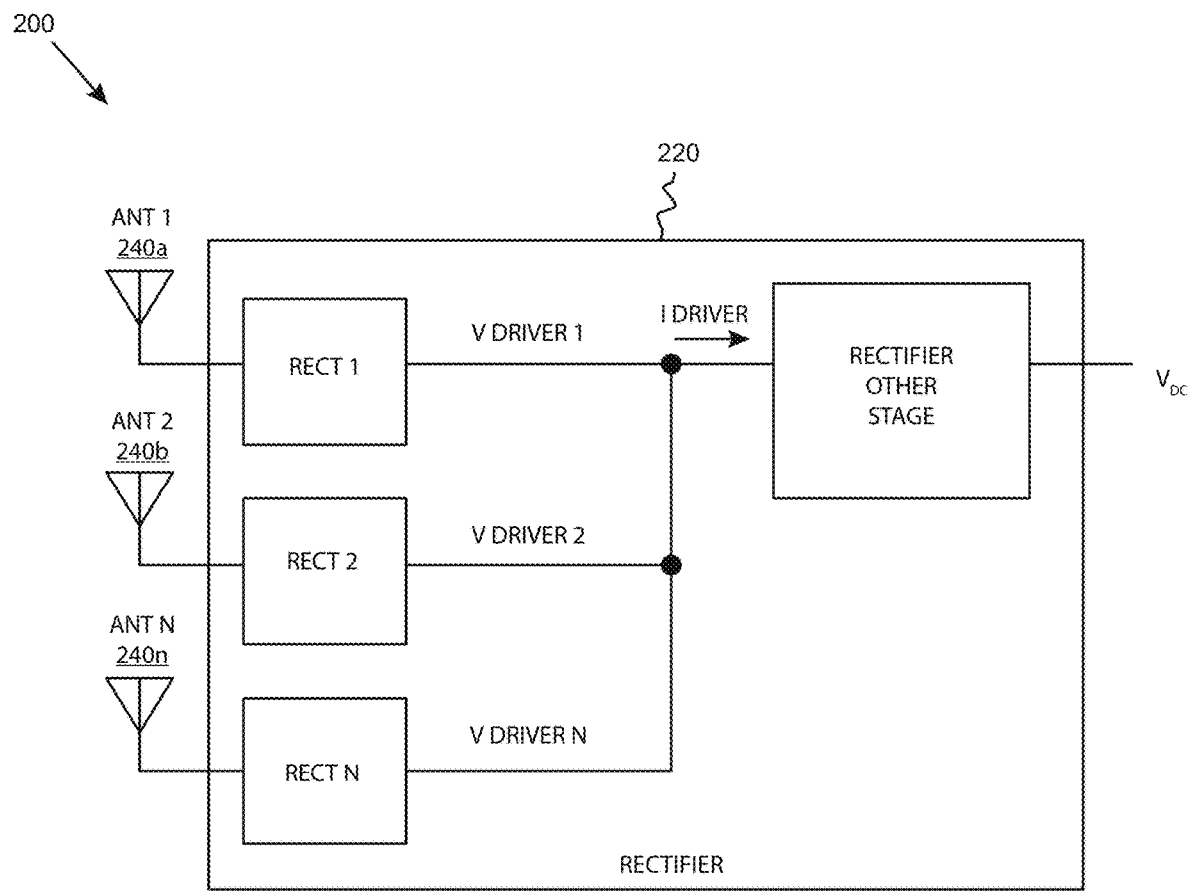
FIG. 11 is a schematic view of a front end circuit configured attached to multiple antennas, consistent with the present inventive concepts.

Integrated circuit 220 (e.g. power management assembly 235) comprises a rectifier that converts a received AC signal (e.g. a power signal transmitted by an external device 500) to a DC voltage that can be used to charge energy storage assembly 270 and/or supply power to the active circuitry of integrated circuit 220 or other active components of implantable device 200. Depending on the induced EMF at antenna 240, and the quality factor, several rectifier topologies can be employed in integrated circuit 220, for example: diode connected metal oxide semiconductor (MOS), native MOS, and/or self-driven synchronous rectifier (SDSR) topologies. The critical tradeoffs for these rectifier topologies are the on-resistance and reverse conduction current, which limit the efficiency of the rectifier. In some embodiments, antenna 240 comprises one or more small loop antennas in the GHz range, and the RF input voltage amplitude is on the order of 300-500 mV, which can be too low for a single rectifier stage to generate sufficient voltage at its output to properly provide power to the on-chip circuitry of integrated circuit 220. In these embodiments, several charge pump-connected rectifier stages can be used to increase the output voltage to a sufficient level. SDSR topology provides reasonable efficiency at low RF amplitudes and is, therefore, suitable for many implantable device 200 configurations. Rectifier efficiency can be optimized by adjusting the number of stages in a voltage multiplier, the capacitance per stage, and/or the size of transistors in each stage (e.g. for a given load). A rectifier topology which supports an antenna 240 comprising multiple antennas is described herebelow in reference to FIG. 11. As shown in FIG. 11, the illustrated rectifier topology combines the output of one of the first stages of the rectifier together. This configuration helps combine the power harvested by each antenna of antenna 240 without a significant increase in antenna 240 loading.

Referring additionally to FIG. 11, in some embodiments, implantable device 200 comprises a rectifier that achieves an efficiency of over 50% when the minimum RF voltage amplitude at the rectifier input is over 300 mV. For example, when antenna 240 receives approximately 500 µW of power, the RF input voltage to the rectifier can be approximately 350 mV. Conventional diode-capacitor ladder rectifiers suffer from low efficiency at low input voltage, especially voltages below 0.5V. To avoid this issue, integrated circuit 220 can comprise one or more charge-pump connected self-driven synchronous rectifiers with low-Vt devices. In one embodiment, the RF front end comprises four stages which are used to boost the voltage sufficiently above 700 mV to ensure proper low dropout (LDO) regulator operation and supply the active circuits of integrated circuit 220. The first stage of the rectifier can be sized larger than one or more subsequent stages (e.g. on the order of 10 times larger), because it drives the current used for recharging energy storage assembly 270, such as to provide sufficient energy for stimulation. This first stage can be configured to output an unregulated voltage of approximately 300 mV-800 mV (e.g. at node $V_{driver}$ of FIG. 11), and can supply approximately 1 mA or more of current depending on the available power and charging rate. The remaining three stages can be sized similarly with respect to each other, and output approximately 900 mV-3200 mV (e.g. at node $V_{DC}$ of FIG. 11) while driving approximately 10-30 µA for the remaining digital and analog circuits of integrated circuit 220. The transistor sizes in the rectifier stages can be optimized to source approximately 10 µA or more. The pump capacitance between stages (e.g. between three stages) can be approximately 5 pF. The efficiency of the rectifier can be approximately 55% or better, after it is sufficiently optimized. Additionally, a smoothing capacitor can be included (e.g. connected to $V_{driver}$ node of FIG. 11) to filter out any leaking RF signal.

Figure 12:
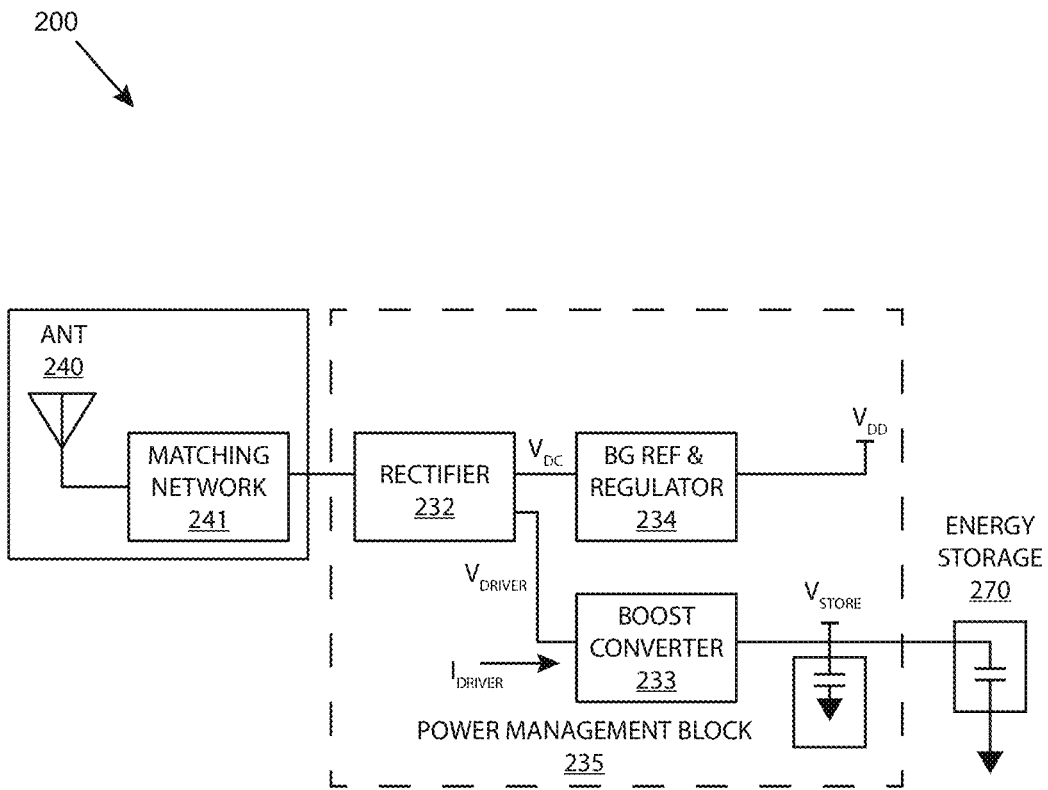
FIG. 12 is a schematic view of a power management assembly configured to store and supply energy, consistent with the present inventive concepts.

Referring additionally to FIG. 12, in some embodiments, implantable device 200 comprises a boost converter that boosts a first rectifier stage output voltage (e.g. $V_{driver}$ of FIG. 12) to a higher voltage (e.g. $V_{store}$ of FIG. 12) to store energy in energy storage assembly 270, which can be configured to at least store stimulation energy for modulation of varies types of tissue, such as nerves, muscles, and/or organ tissue. In some embodiments, one or more implantable antennas 240 each has an associated matching network 241, rectifier 232, boost converter 233, and/or bandgap reference and regulator 234. Implantable device 200 can comprise a demodulator 231a (not shown) as well as the transceiver 231 described herein. In some embodiments, the output voltages from multiple first rectifier stages (e.g. included by and/or connected to multiple antennas 240) are combined in series or parallel. In some embodiments, the output voltages from multiple first rectifier stages are separately provided to the boost converter. The current at which the boost converter charges energy storage assembly 270 (e.g. $I_{driver}$ of FIG. 12) is controlled based on a voltage (e.g. voltage $V_{driver}$ of FIG. 12) to ensure that the voltage does not drop below a threshold (e.g. minimum) voltage, as that voltage drop can cause reduction in the overall energy harvesting efficiency. The monitoring of voltage and current can be utilized to optimize the converter efficiency (e.g. switching frequency, conversion ratio, duty cycle, load current, flying capacitor configuration) based on the operating conditions (e.g. available power and/or input voltage). A variety of boost converter topologies, which are familiar to one skilled in this art, can be used to achieve the boosting function described herein. The boost converter can be partially or completely integrated into integrated circuit 220, it can include some off-chip components, or it can be completely off-chip, depending on the desired level of integration. In an alternative embodiment, a boost converter is positioned at the output of one or more of the later stages to boost voltage for energy storage in energy storage assembly 270. In most cases, the overall efficiency is higher by designing energy harvesting and power management assembly 235 as described hereabove, because the typical rectifier efficiency is lower than a typical boost converter efficiency. Even though a rectifier comprising multiple stages connected in a charge pump configuration performs a similar function to a boost converter by increasing the output voltage with every added stage, the losses increase with the increased number of stages. Therefore, the rectifier efficiency degrades with the increased number of stages. A boost converter, however, can maintain a relatively high efficiency for the desired boosting ratio. Alternative configurations can use a boost converter at the output of any of the other stages of the rectifier or rely on a rectifier to provide sufficient output voltage for temporary energy storage (e.g. in energy storage assembly 270) or direct use (e.g. directly supplied to one or more functional elements 260 such as one or more electrodes configured to deliver electrical energy to tissue to modulate the tissue). The boost converter can also be used with a single rectifier stage and provide the power for the entire functionality of integrated circuit 220.

The output of a last stage of the rectifier can comprise a regulator configured to provide a stable voltage for active circuits in implantable device 200. A key function of the regulator can be to provide a stable supply voltage for circuitry of integrated circuit 220, even as the input voltage or load current experience variations. A linear regulator, switching regulator, or other regulating element (e.g. a voltage regulating element) can be used for this purpose. Linear regulators are simple in design but inefficient for high drop-out voltage with large load currents. Switching regulators can achieve very high efficiency, commonly over 85%, and can regulate to lower, higher, or inverted output voltage as compared to its input. The tradeoff, however, is the complexity in the design of controller 250, and the need for an on-chip clock and large passive components that may need to be off-chip. Various applicable regulator configurations are well known to those of skill in the art. In some instances, it can be desirable to have several different rail voltages, where several separate regulators can be used to provide these voltage rails. Different voltage rails can be achieved by utilizing output from different rectifier stages. Alternative approaches of implementing an efficient DC-DC converter include a switched capacitor converter with adjustable conversion ratio that can be used to set the output voltage to the desired level and avoid the use of a regulator or simplify regulator design criteria. A DC-DC converter with multiple output rails can be implemented in cases where multiple voltages are required for device operation. Magnetics-based DC-DC converters with adjustable configurations (e.g. switching frequency, conversion ratio, duty cycle, and/or switch configurations) can be used to track maximum efficiency point and control the boost ratio.

Both linear and switching regulators require a stable reference voltage, which necessitates either a current or a voltage bandgap reference circuit. Such circuits reject supply noise and are insensitive to ambient temperature by employing proportional and complementary to absolute temperature (PTAT and CTAT) components. Sub-microwatt reference circuits can be employed to avoid the use of bipolar junction transistors or off-chip resistors. These circuits rely on MOS transistors biased in sub-threshold and linear regimes, which are particularly suitable for the application in biomedical devices because of their low power consumption. However, any bandgap reference circuit can be used for creating a reference voltage.

Harvested energy can be stored temporarily in one or more capacitors or rechargeable batteries, such as energy storage assembly 270. In some embodiments, energy storage assembly 270 comprises at least one capacitor, the one or more capacitors charged as described above. A capacitor used for temporary energy storage can be of any kind, such as an electrolytic capacitor or thin film capacitor and can be implemented directly on-chip or off-chip. In some embodiments, it is desirable to use a high density off-chip capacitor or capacitor bank, such as ultra or super capacitors, for temporary energy storage, because of their high capacitance per volume, which allows for small form factor realization of housing 210. In some embodiments, energy may be stored at higher voltages in order to reduce the amount of required capacitance to store a given amount of energy, as can be seen from the following equation for energy stored in a capacitor:

$$E = \frac{1}{2}CV^2$$

In the above equation, E is stored energy, C is capacitance, V is voltage. However, there may be limitations to the maximum voltage at which charge can be stored for a given capacitor, such as a limitation due to the breakdown voltage of the capacitor. Additionally, it may be difficult or undesirable to achieve very high voltages in implantable device 200 because of other considerations, such as safety, device breakdown voltages, DC-DC converter or other system efficiency considerations, etc. Therefore, the highest voltage below the maximum voltage allowed per the above described limitations can be used to store charge, in order to minimize the total required capacitance and, therefore, the volume of the capacitor and size of the implant.

Figure 13:
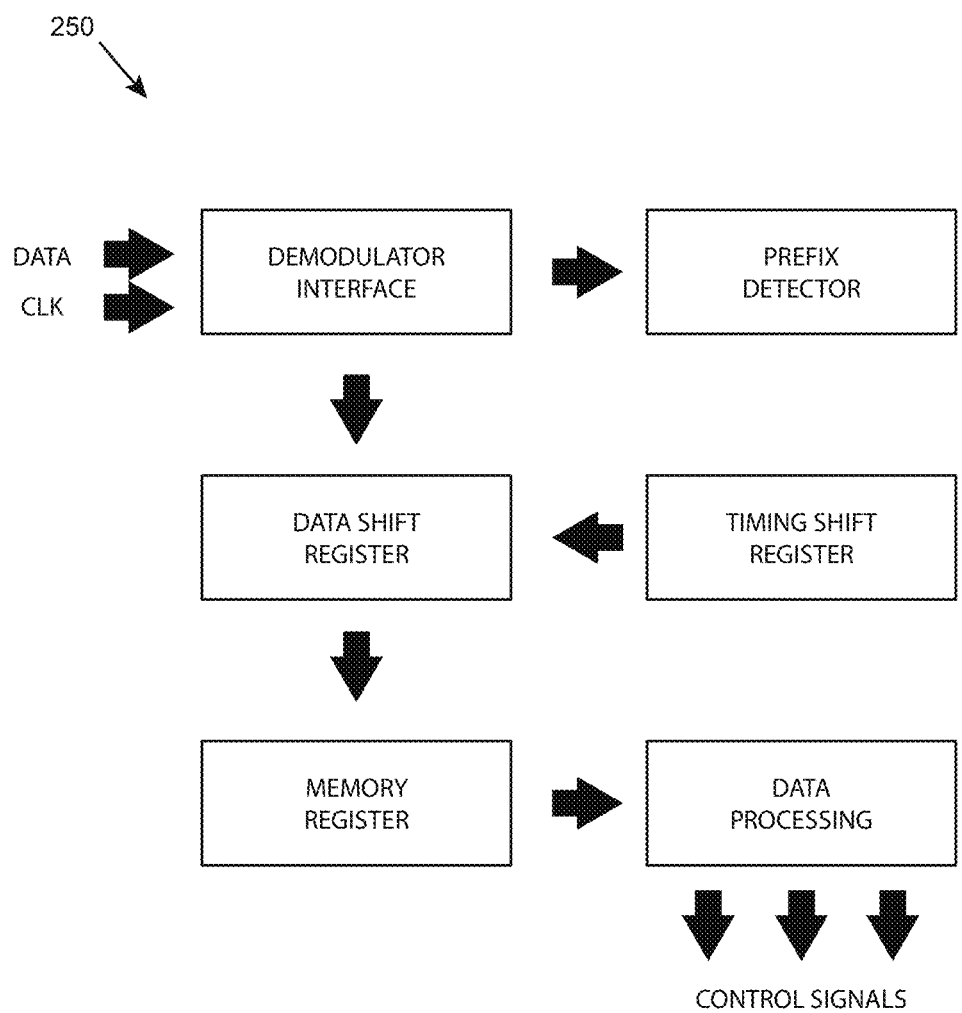
FIG. 13 is a schematic view of a controller that receives data, stores data and processes data, consistent with the present inventive concepts.

Referring additionally to FIG. 13, in some embodiments, controller 250 of FIG. 3 is configured similar to controller 250 of FIG. 13. Controller 250 configures the functionality of implantable device 200. Controller 250 can be configured to interface with both forward and reverse communication circuitry to decode data signals and/or to control the transmission of reverse data. Controller 250 can receive data asynchronously from antenna 240, and store the received data into memory registers of integrated circuit 220. The data can be used to configure the functionality of implantable device 200, including configuring the functionality of pulse generator 280, power management assembly 235, transceiver 231; stimulation interface 262, sensor interface 261, and/or characteristics of one or more communication links. Controller 250 can comprise digital circuitry that operates in stages in order to minimize power overhead. An external device 500 can be configured to provide a device ID and/or data preamble during transmissions to one or more implantable device 200. When the correct device ID and/or data preamble (hereinafter "ID") is received by an implantable device 200, the data capture circuitry is activated and the data packet is shifted into memory. Once a complete set of data is received, digital logic processes the data to configure other elements of implantable device 200. The on-chip circuitry can include one or more configuration parameters that are adjustable, such as to maximize the flexibility of operation of implantable device 200. Controller 250 can provide information necessary to configure these adjustable parameters. The on-chip circuits of integrated circuit 220 which comprise adjustable parameters can include: an RF front end; one or more communication circuits; transceiver 231; power management assembly 235; pulse generator 280; stimulation interface 262 and/or sensor interface 261. The control information for each of these circuits is described in detail herein.

Pulse generator 280 can be configured to generate and deliver one or more electric pulses to tissue, via one or more functional elements 260 (e.g. electrodes), such as to stimulate tissue and/or block neural activity, and/or elicit or suppress muscular activity. Pulse generator 280 can be implemented on integrated circuit 220 and can be implemented with digital and/or analog components. One or more electrical pulses are generated via parameter information provided by controller 250. Pulse generator 280 can be configured to generate a pulse with a desired amplitude, pulse width, frequency, period and/or polarity. Pulses can be delivered by pulse generator 280 continuously and/or intermittently (e.g. duty cycled pulses). In some embodiments, pulse generator 280 can be configured to generate pulses with an adjustable shape. The adjustable shaped pulses can be accomplished by controlling a digital-to-analog converter (DAC) output, such as via controller 250. Pulse generator 280 can be configured to deliver continuous (e.g. DC or other non-pulsed) stimulation. The stimulation parameters can be configured to have a range which is listed in the table below.

| Parameter | Minimum Value | Maximum Value | Step Size |
|---|---|---|---|
| Current amplitude | 0 uA | 10 mA | 100 uA |
| Pulse width | 10 usec | 10 msec | 10 usec |
| Pulse frequency | <0.1 Hz | 100 kHz | |
| Pulse train duty cycle | <1% | 100% | |

Pulse generator 280 can comprise a charge balance module (e.g. charge balance circuitry of integrated circuit 220) configured to avoid accumulation of charge in tissue and/or around a functional element 260/tissue interface (e.g. an electrode/tissue interface). The charge balance circuitry can be implemented using passive circuitry, such as by placing either integrated and/or discrete capacitors of appropriate capacitance in series with one or more functional elements 260 and tissue. In some embodiments, the discrete capacitors are housed in a separate housing, distributed along lead 245, lead 265 and/or interconnect 242. Alternatively or additionally, charge balance circuitry can be implemented using active circuitry, such as by sensing the amplitude, polarity, and time (e.g. by integrating the current) of the delivered energy, which equals the total delivered charge in the stimulation phase as described by the equation below:

$$Q = \int_{t_{start}}^{t_{stop}} I dt$$

where Q is charge, I is current, and t is time. The integration function in the above equation can be implemented in analog domain and/or digital domain, using circuitry known to one who is skilled in this art. During the balancing phase, the current can be delivered in the reverse polarity at a set amplitude which would balance the charge during the remaining portion of the pulse period. The delivered current can be sensed via a resistor in series with one or more functional elements 260. Alternatively or in addition to current sensing, the voltage at the functional element 260/tissue interface can be sensed, and based on the average value of this sensed voltage a DC offset can be added to the stimulation waveform resulting in 0 net DC (average) voltage, forming a feedback loop and balancing delivered charge. In some embodiments, a charge balance circuit comprises a combination of active and passive elements. Numerous other charge balance configurations can be used, such as those known to one skilled in this art. These charge balance configurations are applicable to monophasic, biphasic, and multiphasic stimulation waveforms.

Figure 15:
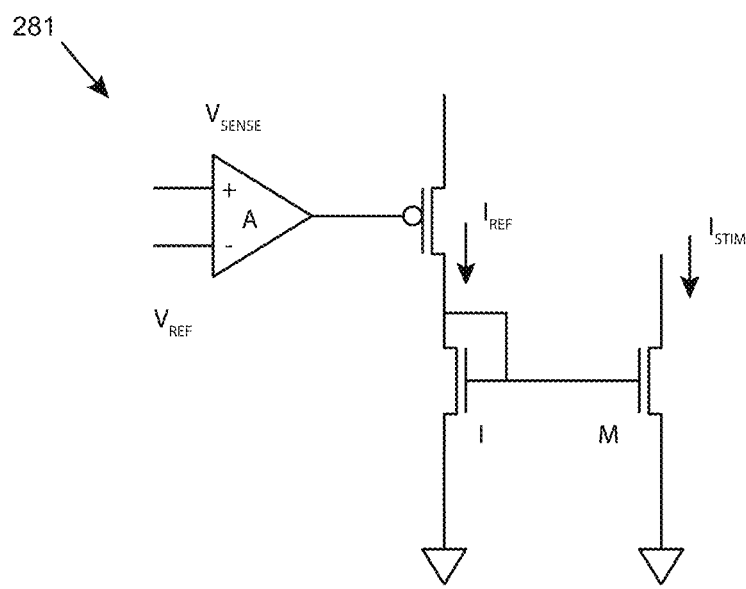
FIG. 15 is a schematic view of a controller configured to control current amplitude in the analog domain, consistent with the present inventive concepts.

Referring additionally to FIG. 15, a pulse generator 280 of an implantable device 200 of the present inventive concepts can comprise pulse amplitude control 281 of FIG. 15. Pulse amplitude control 182 and/or other portions of pulse generator 280 can be implemented on integrated circuit 220, and can comprise a fully digital circuit or a circuit comprising a combination of digital and analog components. Control of the pulse amplitude can be implemented either through voltage or current feedback, and in some cases both may be beneficial. Most stimulation treatments operate based on the amount of current delivered, and the voltage can vary due to a number of factors including the tissue interface, electrode/tissue and tissue impedance, charge storage effects, and the timing, duration, shape and polarity of stimulation pulses. In both cases, however, the controlled quantity of energy delivered can be sensed and/or regulated in a feedback manner. In the case of current amplitude control, the current can be sensed in a variety of ways, such as by sensing voltage across a known series resistance and regulating the current driver strength in order to bring that sensed voltage to a desired value, and thus setting the current to the desired value. In some embodiments of amplitude control loop, an analog error amplifier or a comparator can be used to compare the above mentioned sensed voltage to a set reference value, which can be set by a controller based on the desired amplitude, and in turn can regulate the current driver strength directly, based on the difference between the sensed and desired quantities, as shown in FIG. 15. This configuration achieves a primarily analog method of controlling amplitude. In another configuration, an error amplifier output can be converted to a digital value, fed to controller 250 which can, in turn, digitally control the amplitude, such as through a digital-to-analog converter (DAC) or by turning on or off parallel driver paths. In yet another embodiment, the sensed analog quantity can be converted into a digital value using an analog-to-digital converter (ADC) and this digital value can be fed to controller 250 to control the driver strength, forming mostly a digital way to control (set) the amplitude of pulses generated by pulse generator 280. Other methods to control stimulation amplitude can be implemented.

Figure 14:
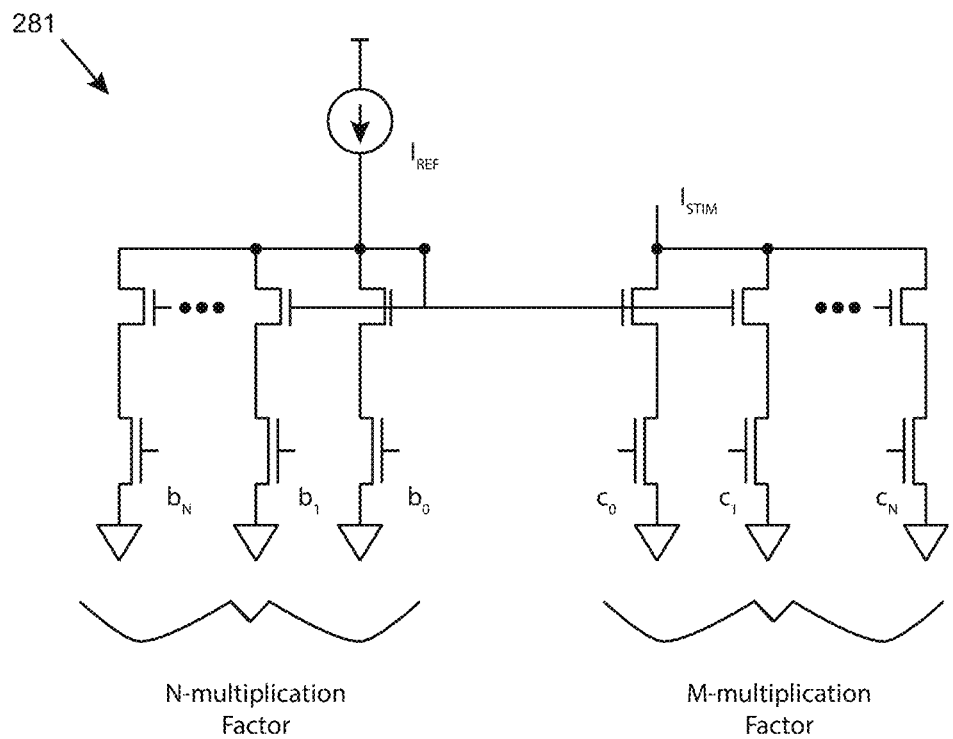
FIG. 14 is a schematic view of a controller configured to digitally control current amplitude, consistent with the present inventive concepts.

Referring additionally to FIG. 14, a pulse generator 280 of an implantable device 200 of the present inventive concepts can comprise pulse amplitude control 281 of FIG. 14. The amplitude of pulses generated by pulse generator 280 can be controlled (set) to the desired value in a variety of ways. In one embodiment, a reference current can be set to a desired value and mirrored using current mirroring techniques. This amplitude control configuration provides a method of setting amplitude with a fixed current mirror ratio. Alternatively, the reference amplitude can be constant and the current mirror ratio can be adjusted instead to set the driver strength to the desired value. The mirror ratio can be controlled on a "mother branch", on a "slave branch", or on both branches, as is shown in FIG. 14. In this configuration, the branches can be identical, linearly weighted, binary weighted, or arbitrarily weighted to achieve a desired degree of resolution in controlling the amplitude. This method of controlling amplitude can also be used for shaping stimulation pulses of pulse generator 280, such as by continuously adjusting the amplitude in discrete steps and/or continuously, such as to achieve a desired pulse shape.

The timing and frequency of pulses generated by pulse generator 280 can be controlled with an on-chip clock, with digital control of timing circuits, and/or from a wirelessly transmitted signal (e.g. a clock signal transmitted by an external device 500). The timing circuits can include circuits based on RC time constants, inverter chains, digital counters, and/or fixed or tunable delay lines. In some instances, more precise timing can be achieved using RC devices, as they tend to be less sensitive to fluctuations in power than digital systems, such as fluctuations associated with a system that is wirelessly powered through tissue. In some instances, timing of the pulses can be controlled using a digital state machine based on counters and a reference clock. The reference clock can either be on-chip, off-chip as in the case of crystal oscillator, or can even be transmitted wirelessly to the implant. Many types of applicable clock generating circuitry are well known to one skilled in the art.

Duty cycling of the pulse trains generated by pulse generator 280 can be achieved using the timing circuits described above or they can be controlled by a controller external to the implantable device 200 (e.g. a controller of an external device 500), depending on the time scale of the therapeutic waveform. If the duty cycling time scale of the pulse trains is too fast or otherwise undesirable for it to be controlled via an external controller (e.g. via a telemetry link), implantable timing circuits can be used to turn the waveform on and off (e.g. timing circuits of controller 250). Alternatively, if the time scale is sufficiently slow or otherwise suitable, an external device 500 can transmit a data packet periodically, with a control signal, to implantable device 200, to control the state of pulse generator 280, turning it either on or off, and achieving the desired duty cycling. The periodically transmitted data packet can act as a "heartbeat" signal (e.g. a periodically transmitted security signal) used in a calibration procedure (e.g. to ensure not only the timing of the therapy is maintained to the desired specification but also the power and data link are operating within the expected quality range). If the "heartbeat" signal is not received by the implant within a specified time window, or the implant does not respond to the "heartbeat" signal within a specified time window, the system can be configured to optimize the power and data link (e.g. adjusting matching network, coupling ratio, operating frequency) or enter a warning state (e.g. issue an alarm or a warning to the patient, such as to allow the patient to adjust the position of external antenna 540 to improve the coupling between external antenna 540 and implantable antenna 240).

Figure 16:
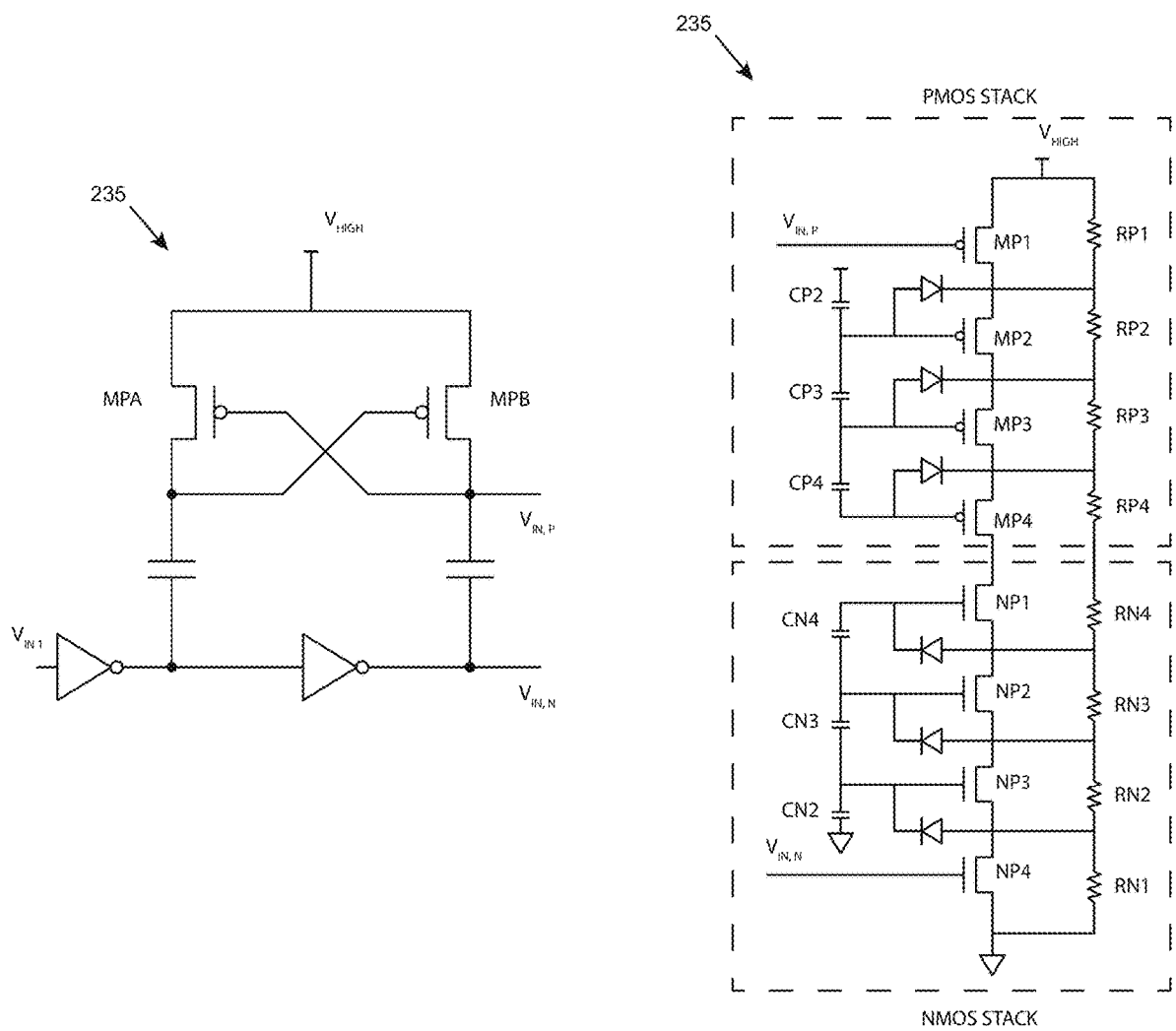
FIG. 16 is a schematic view of a level shifter and a series stack of transistors in push-pull configuration for supporting high voltage operation, consistent with the present inventive concepts.

Referring additionally to FIG. 16, a schematic view of a portion of the power management assembly 235 of an implantable device 200 of the present inventive concepts is illustrated. In some embodiments, one or more portions of the power management assembly 235 of FIG. 2 is of similar construction and arrangement to power management assembly 235 of FIG. 16. Some applications may require a stimulation waveform to have higher amplitude than the breakdown voltage of transistors used to fabricate or implement implantable device 200. In some embodiments, external transistors or transistors fabricated in a different process are used to support these high voltages. This approach requires implantable device 200 to comprise more connections and potentially limits its functionality. Another approach is to use a stacked transistor architecture to handle high voltages (e.g. to electrically connect to a voltage of at least 2V, such as at least 5V, or at least 10V), such as is shown in FIG. 16. The advantage of the stacked transistor architecture is that the high voltage drivers can be integrated in the same process and chip (e.g. integrated circuit 220) as the remaining circuitry, allowing for higher flexibility in design. The driver or the level-shifter for the push-pull stack can be modified to provide independent control of the PMOS and NMOS stack, in order to add the flexibility of disconnecting the output from both high voltage supply and ground. This configuration allows the driver to be in a high impedance state and to neither source nor sink a significant amount of current. Additionally, the individual transistor stacks can have fewer or more series stacked transistors depending on the breakdown voltage and the desired high voltage supply. Alternative configurations for high voltage driver stages can be used to achieve similar functionality.

As described hereabove, implantable device 200 can be configured to sense physiological and/or neural signals from one or more functional elements 260 (e.g. one or more electrodes). Functional elements 260 and stimulation interface 262 can be configured to sense action potentials, neural activity signals, muscular activity signals, and other biological, chemical, biochemical, and/or physiological signals. For electrical signals, electrodes act as transducers to supply a signal to the sensor interface 261. Sensor interface 261 can consist of an optional coupling network, low noise amplifier, variable gain amplifier, tunable filter, and/or ADC to digitize the signal and feed it to controller 250. The above mentioned components make up an analog front end (AFE) for sensor interface 261 and/or stimulation interface 262. In order to enhance versatility of implantable device 200, a majority of the components in the AFE can be configured to have tunable and/or otherwise adjustable parameters which can be wirelessly programmed from an external device 500, and configured by controller 250. For example, the gain of a variable gain amplifier can be adjusted. Low-pass and high-pass cutoff frequencies can be set to desired values in order to accommodate a variety of sensed signals, which may include a higher frequency spectrum than is present in neural activity signals or a lower frequency spectrum contained in physiological action potentials from muscular activity. Additionally, the sampling resolution and frequency can be configured to accommodate a broad range of signals. Depending on the use of the implantable device 200, the sensing AFE can be wirelessly configured to adequately sense the desired signals. Additionally, some or all of the components of implantable device 200 can be turned off and bypassed or just bypassed by sending commands from an external device 500 which configure the AFE. This external adjustment of bypass capability adds additional flexibility in the use of each implantable device 200. Also, the ability to turn on or off individual components of the AFE or AFE in its entirety allows power saving when a component is not being used. In some embodiments, stimulation interface 262 and/or sensor interface 261 can be completely digital, such as an ISP or I2C interface or other digital interface.

One or more functional elements 260 connected to the sensing AFE of sensor interface 261 described above can comprise an electrode, a pressure sensor, an oxygen sensor, a chemical sensor, a biological sensor, a biochemical sensor, a light sensor, a passive transducer, an active transducer, and combinations of one or more of these. The implementation and design of individual components in the sensing AFE are known to those of skill in the art. Some of the signal conditioning components can be omitted from the design or additional components can be added to the design. Additionally, the order of some of the components can be changed, such as placing a filter before a variable gain amplifier. There are corresponding tradeoffs involved in selecting a certain configuration and certain order of components, and these tradeoffs should be obvious to one skilled in the design of interface circuits and analog front end circuits.

Figure 17:
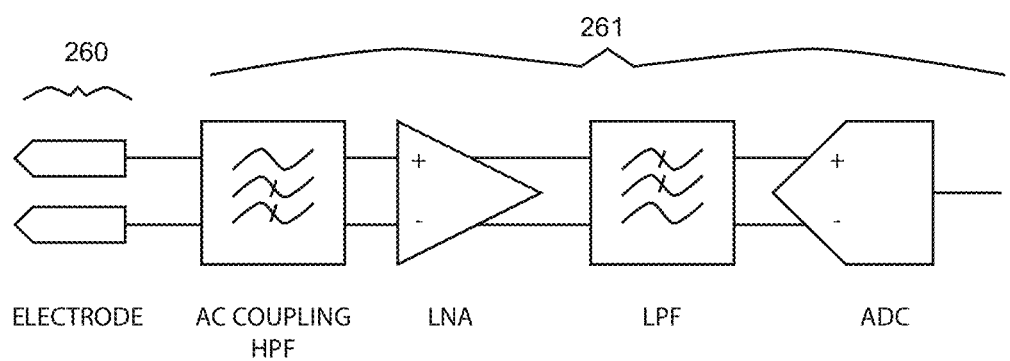
FIG. 17 is a schematic view of sensors and a sensing interface comprising an AC-coupling network, a lower noise amplifier, a low pass filter and an analog-to-digital controller (ADC), consistent with the present inventive concepts.

Referring additionally to FIG. 17, a schematic view of a sensor interface 261 of an implantable device 200 is illustrated, consistent with the present inventive concepts. Sensor interface 261 is attached to two functional elements 260 (e.g. each comprising an electrode). The two functional elements 260 are configured to contact tissue to function as a transducer producing a signal (e.g. voltage difference) related to ionic or electronic current flow in tissue. The produced signal can be further sampled and processed by an analog front end (AFE) of the sensor interface 261 and/or another component of integrated circuit 220. AC-coupling (HPF) components connect to the functional elements 260 (e.g. electrodes) and filter out undesirable low frequency content of the sensed signal. A low noise amplifier (LNA) amplifies the filtered signal to a desired amplitude, and the amplified signal can further be filtered by a low pass filter (LPF). In some embodiments, an additional amplifier may be included after the low pass filter (LPF). The analog signal at the output of low pass filter (LPF) is then converted to a digital signal using an analog-to-digital converter (ADC). Typically, charge-sharing successive approximation ADCs and comparator-based asynchronous binary search ADCs are selected for low power biomedical implantable devices because of their efficient operation, simplicity, and efficient area use compared to other architectures. The sampling frequency and resolution are typically determined based on the desired application. The signal can be sampled asynchronously or through event-driven sampling, which can reduce the required power to recover signals with low temporal activity, as is commonly the case with patient physiological signals. One or more of the parameters of the sensor interface 261 AFE can be made adjustable or otherwise controllable to make the device versatile for a variety of applications and compatible with a variety of transducer-based functional elements 260. For example, the high pass filter and low pass filter cutoff frequencies can be made adjustable by controller 250. Also, the gain of any amplifiers can be made adjustable (e.g. using a variable gain amplifier) and can either be controlled with local feedback or a feedback loop involving one or more external devices 500. The sampling frequency and resolution can also be made adjustable or otherwise controllable, such as by controller 250. One or more of the components of the sensor interface 261 AFE can also be deactivated and bypassed for power savings and versatility. For example, it may be desirable to bypass the AC-coupling (HPF) components and the low noise amplifier (LNA) and simply apply a low pass filter to the signal and convert it to a digital representation, such as if the sensed signal has large amplitude and does not contain a large DC component. This power gating and bypassing can be controlled by the controller 250 and/or by one or more external devices 500 via the data communication described herein. The signal recorded by the one or more functional elements 260 does not have to be converted to a digital representation prior to transmission to one or more external devices 500. Instead, an analog waveform can modulate frequency, phase, and/or amplitude of a carrier signal which is transmitted to the one or more external devices 500 (e.g. when analog modulation is used for data transmission to an external device 500).

Both the sensor interface 261 and stimulation interface 262 can be configured to interface with tissue via one or more functional elements 260. In some embodiments, sensor interface 261 interfaces with one or more functional elements 260 comprising a sensor selected from the group consisting of: an electrode such as an electrode configured to record electrical activity; a pressure sensor; a light sensor; a pH sensor; a blood glucose sensor; a physiologic sensor; and combinations of one or more of these. In some embodiments, stimulation interface circuitry 262 interfaces with one or more functional elements 260 comprising an energy delivery element selected from the group consisting of: an electrode such as an electrode configured to deliver electrical energy to tissue; a light energy delivery element; a sound energy delivery element; a mechanical energy delivery element; an agent delivery element such as an agent delivery element configured to deliver a pharmaceutical agent; and combinations of one or more of these. When one or more implantable devices 200 are configured to deliver neuromodulation energy to tissue, it can be desirable to have the ability to configure one or more functional elements 260 (e.g. electrodes) after implantable device 200 implantation. The configurability can include switching polarity of electrodes, disconnecting electrodes, and/or switching functionality of electrodes from sensing to stimulation. This configurability can be achieved by connecting the functional elements 260 (e.g. electrodes) to stimulation interface 262 and/or sensor interface 261 via a multiplexor (mux) circuit. Controller 250 can be configured to select the desired functional element 260 configuration by applying appropriate select line signals on the mux. In some embodiments, separate stimulation and sensing functional elements 260 (e.g. electrodes) can be used, each of which can be configurable separately. These embodiments may be appropriate when (very) weak input signals are recorded by sensor interface 261 and/or potentially (very) high amplitude stimulation waveforms are delivered by stimulation interface 262 (e.g. which could potentially damage or saturate sensor interface 261).

Data sensed via sensor interface 261 can be processed locally by implantable device 200, transferred to one or more external devices 500 for processing, or it could be partially processed by implantable device 200 and partially by one or more external devices 500 (e.g. depending on the requirements of the desired signal processing algorithms). Implantable device 200 operational parameters (e.g. a stimulation parameter and/or a sensing parameter) can be modified by sensed data (e.g. processed or unprocessed sensed data), via an internal feedback loop and/or via commands sent by external device 500. In some embodiments, the power consumption or complexity requirements of a processing algorithm may be greater than what can be handled by implantable device 200, and the sensor data can be transmitted to one or more external devices 500 for processing and potentially decision making (e.g. adjustment of one or more external device 500 or implantable device 200 stimulation, sensing or other configuration parameters). In some embodiments, the sensor data signal processing can be performed by implantable device 200, limiting the amount of data that needs to be transmitted to an external device 500. Signal processing by implantable device 200 may be preferred in cases where transmissions between external device 500 and implantable device 200 (in either direction) and signal processing performed by external device 500 would consume more power and/or consume more time than processing the signal locally by implantable device 200. Some feedback loops can be designed based on local signal processing by implantable device 200. Other feedback loops that require complex signal processing (e.g. by high speed DSP processors), which are not practical for integration into implantable device 200, can be implemented by implantable device 200 sending raw or partially processed data to external device 500, external device 500 processing the data, and external device 500 transmitting commands or results back to implantable device 200, closing the feedback loop.

In some embodiments, one or more implantable devices 200 are configured to both receive data from and also send data to, one or more external devices 500 (e.g. via a two-way communication link). "Forward transmissions" from an external antenna of external device 500 to an implantable antenna 240 of implantable device 200 provides information for controller 250 of an implantable device 200 to configure the operation of implantable device 200 (e.g. configure a power transmission, data transmission, stimulation and/or sensing parameter). The forward transmission can be performed by external device 500 at speeds up to and in excess of 20 Mbps. Many forms of modulation can be used for data transfer including both amplitude and frequency modulation. In embodiments in which power is also transferred from one or more external devices 500 to one or more implantable devices 200, combining data transmission with power transmission introduces additional challenges. Conventional forms of data modulation can significantly impact the amount of power transferred, and use of multiple antennas or different frequencies would need to contend with large levels of interference from the power carrier. As an alternative, an external device 500 can be positioned to have electrical contact with the surface of the patient's skin, and transmit small electrical signals through the tissue to one or more implantable devices 200. In some embodiments, the external device 500 communication link is combined with the power transfer link in a way that minimizes the effect on power transfer, and operates asynchronously to reduce the overhead on integrated circuit 220. In these embodiments, implantable device 200 and/or external device 500 can be of similar construction and arrangement to what is described in U.S. patent application Ser. No. 13/734,772, titled Method and Apparatus for efficient communication with Implantable Devices, filed Jan. 4, 2013, the content of which is incorporated herein by reference in its entirety. For example, amplitude shift-keying can be used with data encoded in the pulse-width (ASK-PW). In this method, the amplitude of the power carrier is modulated with minimal depth, which minimizes the impact on power delivery to the implantable device 200 as desired. Data is encoded in the width of transmitted pulses, allowing for asynchronous operation on the implant, which can reduce the complexity of the on-chip circuitry of integrated circuit 220. By eliminating the need for carrier synchronization circuitry, the power consumption of implantable device 200 is also minimized. This method can also easily accommodate variable data rates and modulation depth, which gives flexibility in its overall power consumption and also can increase robustness when the antenna link is weaker.

Figure 18:
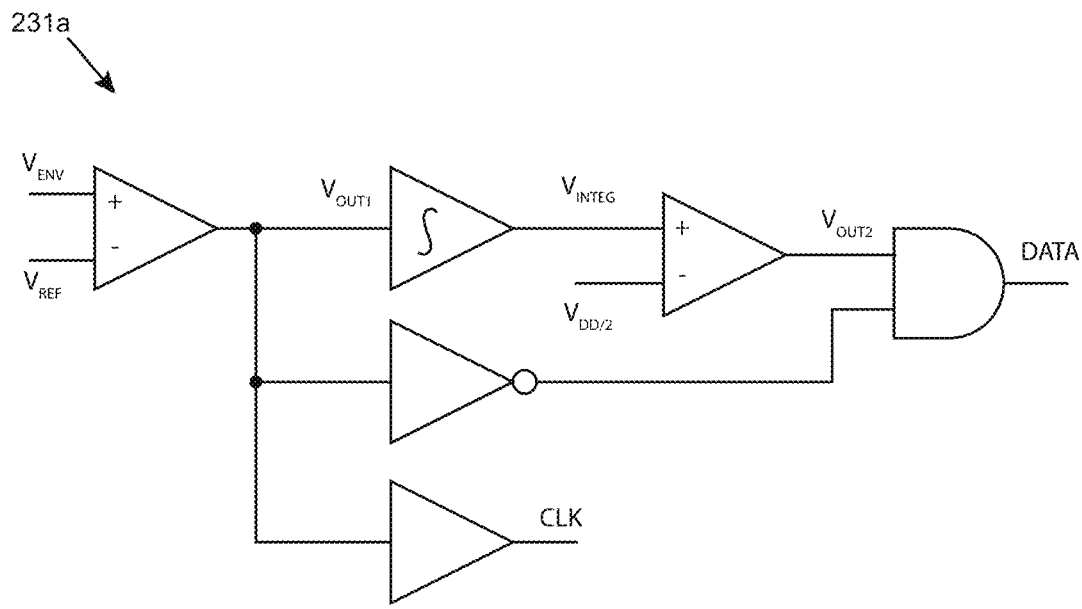
FIG. 18 is a time versus signal chart of a communication system of an external system configured for amplitude shift keying (ASK) with data encoded in the pulse width modulation scheme, consistent with the present inventive concepts.
Figure 18:
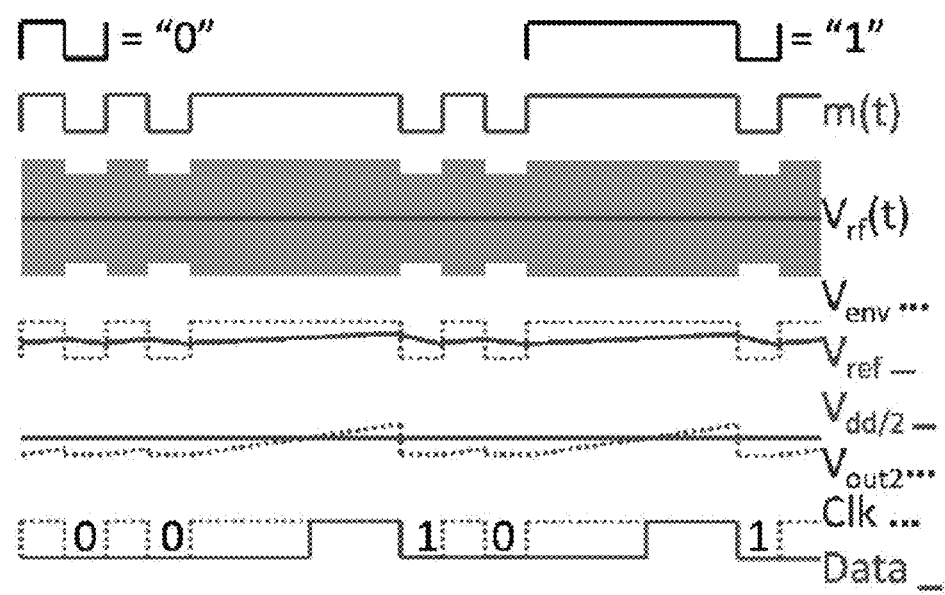

Referring additionally to FIG. 18, a high-level diagram of this method is illustrated, consistent with the present inventive concepts.

Figure 19:
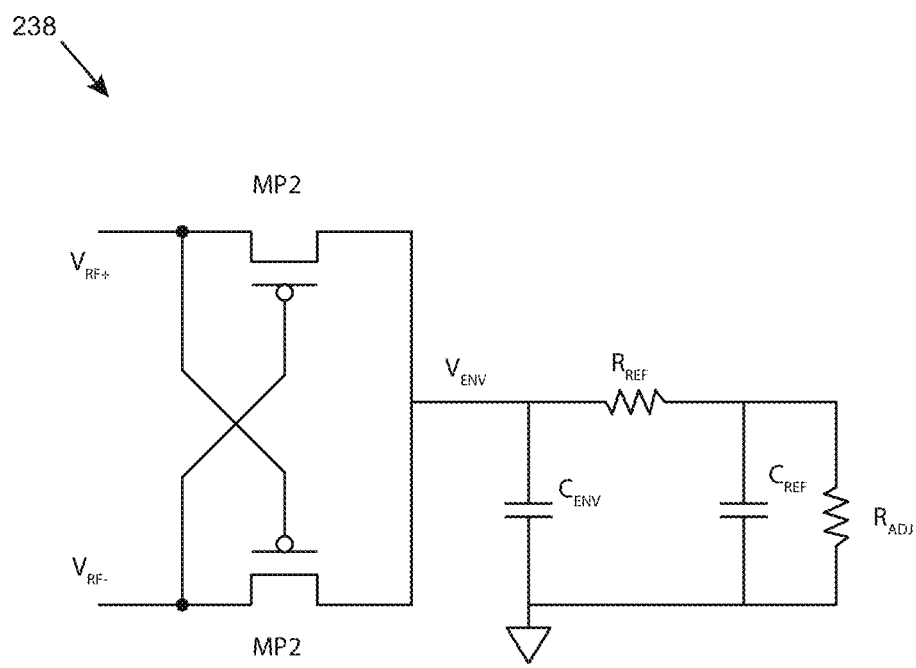
FIG. 19 is a schematic view of an envelope detector with a dynamic reference generator for converting a modulated envelope into a digital signal, consistent with the present inventive concepts.

Referring additionally to FIG. 19, a schematic of an envelope detector is illustrated, consistent with the present inventive concepts. In some embodiments, each implantable antenna 240 comprises an envelope detector. The envelope detector extracts the envelope of the power carrier, and the resulting signal is converted to a full-swing digital signal through a comparator. The envelope detector uses a dynamic reference to extract the desired signal because of the inherent fluctuations from wireless powering, and the operation of this system is shown in FIG. 19. The digital signal can include both long and short pulses that can be recovered from the envelope of the power carrier, and these pulses can be integrated to determine the encoded data. The falling edge of the pulse can be used to clock the data as shown in the figure, and this clock signal can be repurposed for other uses on the chip as well. The diagram of FIG. 18 also depicts the waveforms of the signals, showing the transmitted envelope, the digital version of the envelope, and the method for extracting data from the pulse width.

One or more implantable devices 200 can comprise an implantable transmission module configured to transmit data to one or more external devices 500. Each implantable antenna 240 can comprise or otherwise be associated with an implantable transmission module (e.g. a separate transmission module for each implantable antenna 240). The transmission module can comprise a backscattering link, an active transmitter, and/or a body conduction-based transmitter, as described herein. The reverse data transfer from an implantable device 200 to one or more external devices 500 can operate in conjunction with the forward data transfer link, and can be capable of data transmission speeds up to and exceeding 2 Mbps. Integrated circuit 220 can comprise an oscillator for an active transmitter that sends data back to an external device 500. This configuration would require significant power of implantable device 200 to operate and may need to contend with interference from the power carrier. Even with these challenges, these oscillator implementations may have advantages in certain situations. One potential configuration with a smaller power budget includes a backscattering link, in which the loading at antenna 240 is altered to introduce mismatch, which can then be sensed by an antenna of external device 500. The loading can be varied to adjust one or more of: backscattered signal amplitude and phase; backscattered signal pulse width; data rate; and combinations thereof. This backscattering configuration is similar to what is used in commercial RFID systems, though transmitting through tissue poses a different set of challenges. This configuration can be sensitive to environment changes, and these variations are common when operating in tissue. To mitigate the effects of the operating environment, several possible loads can be included, and the load that maximizes the received signal can be selected or otherwise used. This load satisfies two requirements: maximizing the average backscattered power per bit ($\max\{\sigma_1+\sigma_2\}$) and maximizing the Euclidean distance between the reflection coefficients on the Smith chart corresponding to the matched and mismatched loads ($\max\{|\Gamma_1-\Gamma_{2,k}|\}$). In this description, $\sigma$ corresponds to the termination-dependent implant antenna radar cross-section and $\Gamma$ are the reflection coefficients corresponding to matched termination and terminated with some load, k.

Another configuration for an implantable transmission module sending data from an implantable device 200 to one or more external devices 500 (i.e. reverse communication) uses one or more functional elements 260 (e.g. one or more electrodes also configured to deliver stimulation energy to tissue) to transmit a small (e.g. not significantly stimulating) signal through the patient's tissue. In these configurations, an external device 500 includes some form of electrical connection with the surface of the patient's skin to detect the small fluctuations in electrical stimulation sent by implantable device 200. This configuration has potential advantages in that it requires very low-power from implantable device 200, and can operate at frequencies where there won't be interference with power and/or data transmissions from an external device 500 to one or more implantable devices 200. Additionally, data transmitted by an implantable device 200 in this configuration can be performed asynchronously and simultaneously with forward data transfer, whereas backscattering modulation and active transmission through antenna 240 of an implantable device 200 would be very limited in this type of simultaneous operation. Because there is little or no interference, external device 500 can have a very sensitive receiver, which means that the electrical signals sent through the tissue can be very small (even below <1% of the delivered therapeutic stimulation). If there are multiple implantable devices 200, this configuration would allow for rapid communication between one or more implantable devices 200 and one or more external devices 500. The communication signal can be configured to be charge balanced with a body conduction reverse data communication approach to ensure safe operation mechanism, similar to the neuromodulation interface approach described hereinabove. The charge balance can be active, as described above, can be passive, by utilizing AC-coupling capacitors and/or resistors configured to remove access charge, or can be a combination of active charge balance with AC-coupling capacitors and/or parallel resistors eliminating the residual DC offset. When one or more implantable devices 200 are configured to receive transmissions from a single external device 500, the external device 500 position with respect to the one or more implantable devices 200 can be optimized based on the link gain quality received from the one or more implantable devices 200. Using a body conduction reverse communication link, each implantable device 200 can encode its transmitted signal using code domain multiple access (CDMA) in order to avoid data collision. Therefore, multiple implantable devices 200 could transmit "data beacons" asynchronously to the external device 500.

For both the forward and reverse communication configurations between one or more implantable devices 200 and one or more external devices 500, the data transfer needs to be safe, reliable, private, and unaffected by erroneous or intentional (e.g. malicious tampering) outside interferences. The ASK-PW method for forward data transfer offers advantages in safety because it minimizes effects on power delivery, allowing for higher power transfer efficiency and therefore less tissue heating due to the power carrier. The interaction with the implantable device 500 is also protected in that the transmitted data must be sent on the power signal, which must be placed proximate the surface of the skin (i.e. proximate the antenna 240 of implantable device 200) to send sufficient power for operation. This close proximity results in a very high signal-to-noise ratio (SNR) that reduces effects of interference from other types of electromagnetic radiation that could disturb the operation of the implantable device 200. Additionally, each implantable device 200 only operates (e.g. delivers stimulation energy) when verified data is received, ensuring that implantable device 200 is inactive when not given specific instructions. The data sent from implantable device 200 to an external device 500 is kept private because receiving of the data requires an external antenna 540 of external device 500 to be in very close proximity to implantable device 200, preventing other devices or antennas from detecting the data signal. The communication protocols can be unique and can include encryption to further ensure privacy and/or prevention of tampering.

For both the forward and reverse communication links, the data transfer can be transferred digitally, and thus numerous forms of error detection and/or correction can be implemented, such as via a data confirmation module of an implantable device 200, an external device 500 and/or another component of apparatus 10. The error detection and/or correction can be accomplished through repetition codes, parity bits, checksums, error correcting codes, and/or other methods. For the forward data link (transmissions from an external device 500 to one or more implantable devices 200), some embodiments, a data confirmation module includes an ID code and/or a unique preamble that must be present before data capture starts. Once the data capture phase completes, error detection and/or correction can be performed for additional protection against errors. For the reverse data link (transmissions from an implantable device 200 to one or more external devices 500), there can be significantly more errors because of the difficulty of low-power communication through tissue environments. In these cases, error correction by the data confirmation module could be essential, and any of the previous correction methods can be used. The external device 500 can comprise a data confirmation module that acknowledges the data through a handshake protocol with implantable device 200, and/or requests that data be resent by implantable device 200 if errors are detected or otherwise to ensure proper receipt of data. In some embodiments, apparatus 10 comprises a data confirmation module configured to confirm one or more of: transferred data; communication protocol; modulation method; device ID; data preamble; parity codes; encrypting; encoding; and combinations thereof. In some embodiments, apparatus 10 comprises a data confirmation module configured to confirm the integrity of information selected from the group consisting of: transferred data; communication protocol; modulation method; device ID; data preamble; parity codes; encrypting; encoding; variable modulating loads; and combinations thereof. In some embodiments, apparatus 10 comprises a data confirmation module comprising a function selected from the group consisting of: handshaking protocol; error checking; reverse data transmission; error correction; repetition codes; parity codes; encryption; communication protocol; encoding; device ID; preamble; and combinations thereof.

The apparatus 10 of the present inventive concepts comprising at least one external device 500 and at least one implantable device 200 is highly reconfigurable to a variety of uses in a variety of anatomical sites. Because of apparatus 10's highly reconfigurable and versatile nature, one or more implantable devices 200 can be programmed wirelessly to deliver various therapeutic stimulation parameters, which can depend on what organs, nerves, muscles, and/or other tissues each implantable device 200 is intended to stimulate. For example, some of the known neuromodulation treatments for which the apparatus 10 of the present inventive concepts can be used include but are not limited to: medically refractory angina; brain-computer interface for movement disorders; cancer pain treatment; chronic critical limb ischemia; complex regional pain syndrome; deep brain stimulation for a variety of neurologic disorders; medically refractory epilepsy; failed back surgery syndrome; fecal constipation; fecal incontinence; urinary incontinence and other urologic disorders; a variety of gastric disorders such as GERD, chronic indigestion, gastroparesis; obesity; hepatic stimulation for diabetes management; gastric stimulation for satiety; stomach emptying regulation; food transit acceleration or slowing down through gastrointestinal tract; medically refractory headaches; migraine treatment; neuropathy; neuropathic pain; painful peripheral neuropathy; pelvic floor dysfunction; Parkinson's disease; Spasticity; Spinal Cord Stimulation; Vagus Nerve Stimulation; Gastric Electrical Stimulation; Sacral Nerve Stimulation; and combinations of one or more of these. Each implantable device 200 can stimulate nerves to activate them, inhibit their activity, and/or block propagation of neural signaling. Additionally, each implantable device 200 can be configured to activate or suppress other tissue or cellular activity including certain muscles or muscle groups, and each can inhibit muscular activity and/or cause their relaxation. Therefore, each implantable device 200 can be used to exercise certain muscles to increase their tone and restore or improve their functionality, serving as a rehabilitative tool. Other types of neuromodulation for which the apparatus of the present inventive concepts can be used include but are not limited to: auditory brainstem stimulation; occipital nerve stimulation; peripheral nerve stimulation; other functional electrical stimulation; and combinations of one or more of these.

Additionally, because of the sensing ability of each implantable device 200, the apparatus of the present inventive concepts can be used as a diagnostic tool to monitor physiological activity; neural activity; muscular activity; chemical activity; biological activity; biochemical activity; and combinations of one or more of these. Additionally, depending on the included functional elements 260 (e.g. sensors), each implantable device 200 can monitor its surrounding environment pH levels, pressure, temperature, impedance, radioactivity, oxygen content, and/or other conditions proximate each implantable device 200.

The apparatus 10 of the present inventive concepts can monitor impedance during or outside of stimulation in order to keep track of the functional element 260/tissue interface status (e.g. electrode/tissue interface status) to ensure the contact (e.g. electrical connection) with tissue remains acceptable. The impedance can be monitored by driving current through tissue and measuring voltage across a known resistor value which is placed in series with one or more functional elements 260, thus measuring the amplitude of stimulation current, and by measuring the voltage difference between the functional elements 260 (e.g. between electrodes). The magnitude of impedance can be calculated from the measured values of stimulation current and voltage. Additionally, relative phase of current can be measured with respect to voltage phase for a given applied stimulation tone to derive the phase of impedance. Alternatively, the delay between applied voltage and current can be measured to derive the phase information.

Integrated circuit 220 can comprise various components as described herein. In some embodiments, integrated circuit 220 comprises one or more components selected from the group consisting of: power-on-reset circuit (POR); calibration circuits; memory, timing and delay circuits; other circuits; and combinations of one or more of these.

In some embodiments, the transmitter 530 of an external device 500 transfers electromagnetic energy to one or more implantable devices 200 at frequencies in the low-GHz range. This frequency range has advantages for antennas 240 of implantable device 200 comprising very small antennas that receive power in tissue environments. The one or more external antennas 540 can also be reduced in size and optimized to improve link gain. The one or more external antennas 540 can be designed to focus energy delivery, similar to a beamforming or beam steering approach. Additionally, the low-GHz frequency operation desensitizes the link gain to the relative position, orientation, and alignment of the external antenna 540 with respect to the implantable antenna 240, allowing for a more robust system and operation of multiple implantable devices 200 with a single external device 500. The carrier frequency can be generated in a number of configurations, such as those including oscillators or signal generators. This carrier is then modulated by introducing a controllable impedance in the RF path to introduce mismatch (e.g. impedance mismatch) and therefore controllably altering the amplitude of the transmitted signal. This method can be easily implemented with transmission lines and transistors. One implementation uses a BJT transistor tied to the RF path with a transmission line to ground, and by controlling the voltage at the base of the transistor, a variable impedance can be introduced. This method can modulate the amplitude between 0-100%. Lower amplitude shift keying modulation depths have a minimal effect on power transfer, however data can be received more robustly with larger amplitude modulation depths. The signal can be amplified after modulation and then transmitted through external antenna 540 (e.g. one or more external antennas). Introducing controllable mismatch to modulate the carrier prior to amplification introduces minimal inefficiencies in the system, since the signal power amplitude is very low before amplification. External antenna 540 will be matched to the frequency of the carrier to maximize the radiated electromagnetic energy. For an implantable device 200 with backscattering data links, this external antenna 540 can be capable of sensing small amounts of reflected energy and recovering the intended information. Alternatively, for implantable devices 200 transferring data with small electrical signals transferred through tissue, each external device 500 can include electrical contacts with the surface of the skin to sense and recover these signals.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth hereinbelow not be construed as being order-specific unless such order specificity is expressly stated in the claim.

What is claimed is:

1. A medical apparatus for a patient, comprising:
    an external system configured to transmit one or more transmission signals, each transmission signal comprising at least power or data; and
    an implantable system configured to receive the one or more transmission signals from the external system;
    wherein the external system comprises a first external device comprising:
        at least one external antenna configured to transmit a first transmission signal to the implantable system, the first transmission signal comprising at least power or data,
    wherein the first external device transmits a periodic security signal to a first implantable device; and
    wherein the implantable system comprises the first implantable device comprising:
        at least one implantable antenna configured to receive the first transmission signal from the first external device;
        at least one implantable transmission module configured to transmit data to the external system; and
        a variable load connected to the at least one implantable antenna, wherein data is transmitted by varying the load,
    wherein the medical apparatus is configured to at least one of neuromodulate tissue or record patient information,
    wherein the medical apparatus is configured to provide asynchronous transfer of data between the external system and the implantable system,
    wherein the periodic security signal is used by the first implantable device in a calibration routine to ensure that at least one of a timing of the neuromodulation is maintained to a desired specification or the first transmission signal is operating within an expected quality range, and
    wherein the medical apparatus is configured to enter a warning state when one or more of the following conditions occur: the first implantable device does not reply to the periodic security signal; the first implantable device does not receive the periodic security signal; and combinations thereof.

2. The medical apparatus according to claim 1, wherein the external system is configured to transmit power and data to the implantable system, and wherein the data is transmitted to the implantable system by combining a power carrier with a data signal.

3. The medical apparatus according to claim 1, wherein the external system transmits data to the implantable system using ASK modulation.

4. The medical apparatus according to claim 3, wherein the first external device transmits an ASK modulated signal to the first implantable device, and wherein data is encoded in the pulse width.

5. The medical apparatus according to claim 4, wherein the data transmission is reconfigurable.

6. The medical apparatus according to claim 1, wherein the apparatus is configured to provide configurable transfer of data between the external system and implantable system.

7. The medical apparatus according to claim 6, wherein the apparatus is configured to provide configurable transfer of data from the external system to the implantable system.

8. The medical apparatus according to claim 6, wherein the data transfer comprises an adjustable parameter selected from the group consisting of: data rate; pulse width; modulation depth; and combinations thereof.

9. The medical apparatus according to claim 1, wherein the apparatus is configured to provide two-way communication between the first external device and the first implantable device.

10. The medical apparatus according to claim 1, wherein the apparatus comprises closed-loop feedback configured to adapt performance of the apparatus in real-time.

11. The medical apparatus according to claim 1, wherein the apparatus comprises closed-loop feedback configured to adapt performance of the apparatus in real-time.

12. The medical apparatus according to claim 11, wherein the apparatus comprises a treatment parameter, and wherein the treatment parameter is adjusted based on the closed-loop feedback.

13. The medical apparatus according to claim 12, wherein the treatment parameter is adjusted based on performance of the first implantable device.

14. The medical apparatus according to claim 12, wherein the treatment parameter is adjusted based on a change in a patient parameter.

15. The medical apparatus according to claim 1, wherein the first external device comprises a unique ID.

16. The medical apparatus according to claim 1, wherein the first external device is configured to adjust a stimulation waveform delivered by the first implantable device.

17. The medical apparatus according to claim 1, wherein apparatus is configured to provide a treatment for medically refractory angina, a movement disorder, pain treatment, cancer pain treatment, chronic critical limb ischemia, complex regional pain syndrome, deep brain stimulation, medically refractory epilepsy, failed back surgery syndrome, fecal constipation, fecal incontinence, urinary incontinence, a urologic disorder, a gastric disorder, GERD, chronic indigestion, gastroparesis, obesity, diabetes, medically refractory headaches, migraine treatment, neuropathy, neuropathic pain, peripheral neuropathy, pelvic floor dysfunction, Parkinson's disease, spasticity, or combinations thereof.

18. The medical apparatus according to claim 1, wherein the apparatus is configured to provide spinal cord stimulation, vagus nerve stimulation, gastric stimulation, sacral nerve stimulation, auditory brainstem stimulation, occipital nerve stimulation, peripheral nerve stimulation, or combinations thereof.

19. The medical apparatus according to claim 18, wherein the stimulation provides one or more of: nerve activation, inhibition of nerve activity, and inhibition of propagation of neural signaling.

20. The medical apparatus according to claim 1, wherein the periodic security signal comprises a control signal configured to control the state of the implantable device.

21. The medical apparatus according to claim 1, wherein the calibration routine ensures that the timing of the neuromodulation is maintained to a desired specification.

22. The medical apparatus according to claim 1, wherein the medical apparatus is configured to enter a warning state when one or more of the following conditions occur: the first implantable device does not reply to the periodic security signal within a specified time window; the first implantable device does not receive the periodic security signal within a specified time window; and combinations thereof.

* * * * *